US009235039B2

(12) United States Patent
Lee

(10) Patent No.: US 9,235,039 B2
(45) Date of Patent: Jan. 12, 2016

(54) BROAD-SPECTRUM ILLUMINATOR FOR MICROSCOPY APPLICATIONS, USING THE EMISSIONS OF LUMINESCENT MATERIALS

(71) Applicant: DiCon Fiberoptics, Inc., Richmond, CA (US)

(72) Inventor: Ho-Shang Lee, El Sobrante, CA (US)

(73) Assignee: DiCon Fiberoptics Inc., Richmond, CA (US)

( * ) Notice: Subject to any disclaimer, the term of this patent is extended or adjusted under 35 U.S.C. 154(b) by 126 days.

(21) Appl. No.: 14/072,567

(22) Filed: Nov. 5, 2013

(65) Prior Publication Data
US 2014/0233095 A1    Aug. 21, 2014

Related U.S. Application Data

(60) Provisional application No. 61/765,279, filed on Feb. 15, 2013.

(51) Int. Cl.
*G02B 21/06* (2006.01)
*G02B 21/00* (2006.01)
*G01N 21/64* (2006.01)

(52) U.S. Cl.
CPC ............ *G02B 21/06* (2013.01); *G01N 21/6458* (2013.01); *G02B 21/0076* (2013.01)

(58) Field of Classification Search
CPC ........... G02B 21/06; H05B 37/02; F21V 9/00
USPC ........ 359/385–390; 362/249.02, 311.02, 231, 362/233, 268
See application file for complete search history.

(56) References Cited

U.S. PATENT DOCUMENTS

| | | |
|---|---|---|
| 4,519,020 A | 5/1985 | Little |
| 4,739,456 A | 4/1988 | Little |
| 4,843,528 A | 6/1989 | Pearce-Harvey et al. |
| 5,012,609 A | 5/1991 | Ignatius et al. |
| 5,165,778 A | 11/1992 | Matthias et al. |
| 5,235,499 A | 8/1993 | Bertenshaw |
| 5,687,062 A | 11/1997 | Larson |
| 5,715,040 A | 2/1998 | Iba |
| 6,092,914 A | 7/2000 | Esakoff et al. |

(Continued)

OTHER PUBLICATIONS

Notice of Allowance and Fees Due for U.S. Appl. No. 14/071,334 mailed Dec. 24, 2014, 22 pages.

(Continued)

*Primary Examiner* — Frank Font
(74) *Attorney, Agent, or Firm* — Davis Wright Tremaine LLP

(57) ABSTRACT

A broad-spectrum, multiple wavelength illuminator comprises a luminescent body, and a plurality of semiconductor chips spaced apart from the luminescent body emitting light within one or more wavelength ranges towards the luminescent body, causing the luminescent body to emit light of one or more wavelength ranges. An optical element adjacent to the luminescent body collects light emitted by the luminescent body. An optical device collects light collected by the optical element. An aperture located between the optical element and the optical device passes the light emitted by the luminescent body along an optical axis, wherein light collected by the optical element and the optical device and passed by the aperture forms a beam of light illuminating a target. Alternatively, instead of being spaced apart from the chips, the luminescent body may be a layer adjacent to the chips.

28 Claims, 15 Drawing Sheets

(56) References Cited

U.S. PATENT DOCUMENTS

| | | |
|---|---|---|
| 6,504,301 B1 | 1/2003 | Lowery |
| 6,554,450 B2 | 4/2003 | Fang et al. |
| 6,659,622 B2 | 12/2003 | Katogi et al. |
| 6,690,509 B2 * | 2/2004 | Vodyanoy et al. ............ 359/368 |
| 6,809,347 B2 | 10/2004 | Tasch et al. |
| 6,860,619 B2 | 3/2005 | Swanson |
| 6,866,401 B2 | 3/2005 | Sommers et al. |
| 6,921,182 B2 | 7/2005 | Anderson et al. |
| 7,140,751 B2 | 11/2006 | Lin |
| 7,173,383 B2 | 2/2007 | Vornsand et al. |
| 7,192,162 B2 | 3/2007 | Tanaka et al. |
| 7,220,018 B2 | 5/2007 | Crabb et al. |
| 7,261,438 B2 | 8/2007 | Alessio |
| 7,295,379 B2 | 11/2007 | Tsai |
| 7,543,952 B1 | 6/2009 | Chang |
| 7,549,772 B2 | 6/2009 | Wang |
| 7,670,030 B2 | 3/2010 | Klipstein |
| 7,676,915 B2 | 3/2010 | Ter-Hovhannissian |
| 7,722,211 B2 | 5/2010 | Marra et al. |
| 7,771,088 B2 | 8/2010 | Chen |
| 7,832,894 B2 * | 11/2010 | Rudolph et al. .............. 362/231 |
| 7,893,445 B2 | 2/2011 | van de Ven et al. |
| 8,038,319 B2 | 10/2011 | Bailey |
| 8,044,427 B2 | 10/2011 | Su et al. |
| 8,047,684 B2 | 11/2011 | Chang |
| 8,057,060 B2 | 11/2011 | fredricks |
| 8,508,127 B2 | 8/2013 | Negley et al. |
| 8,523,385 B2 | 9/2013 | Lu et al. |
| 8,568,009 B2 | 10/2013 | Chiang et al. |
| 8,596,815 B2 | 12/2013 | Lee et al. |
| 8,740,663 B2 | 6/2014 | Kim et al. |
| 2005/0152146 A1 | 7/2005 | Owen et al. |
| 2005/0237747 A1 | 10/2005 | Shimizu et al. |
| 2007/0058368 A1 | 3/2007 | Partee et al. |
| 2007/0253196 A1 | 11/2007 | Ormiston |
| 2008/0218995 A1 | 9/2008 | Gilkey et al. |
| 2008/0239476 A1 * | 10/2008 | Matz et al. .................... 359/389 |
| 2009/0080184 A1 | 3/2009 | Kobilke |
| 2009/0190363 A1 | 7/2009 | McDonnell et al. |
| 2009/0201577 A1 | 8/2009 | LaPlante et al. |
| 2009/0288340 A1 | 11/2009 | Hess |
| 2009/0315062 A1 | 12/2009 | Su et al. |
| 2010/0033970 A1 | 2/2010 | Jetter et al. |
| 2010/0188018 A1 | 7/2010 | Salm |
| 2011/0050126 A1 | 3/2011 | Wang et al. |
| 2012/0044713 A1 | 2/2012 | Chiang et al. |
| 2012/0176769 A1 * | 7/2012 | Reimer et al. .................. 362/84 |
| 2013/0277643 A1 * | 10/2013 | Williamson et al. ............ 257/13 |
| 2013/0314893 A1 * | 11/2013 | Paquette ........................ 362/84 |
| 2013/0335989 A1 * | 12/2013 | Sato et al. ..................... 362/510 |
| 2014/0027789 A1 * | 1/2014 | Katona et al. .................. 257/79 |
| 2014/0092362 A1 * | 4/2014 | Narayanaswamy et al. .. 351/221 |

OTHER PUBLICATIONS

U.S. Final Office Action for U.S. Appl. No. 13/216,085 mailed May 14, 2014, 27 pages.

Notice of Allowance and Fees Due for U.S. Appl. No. 13/216,085 mailed Nov. 7, 2014, 8 pages.

U.S. Office Action for U.S. Appl. No. 13/756,282 mailed Nov. 20, 2014, 7 pages.

Koninklijke Philips Electronics N.V., "Intellectual Property & Standards, Licensing Programs, LED-based Luminairies and Retrofit Bulbs", Nov. 11, 2010; www.ip.philips.com/services, 2 pages.

Koninklijke Philips Electronics N.V., "Philips Color Kinetics Core LED Lighting Technologies", Nov. 11, 2010; www.colorkinetics.com/technologies/core, 2 pages.

U.S. Office Action for U.S. Appl. No. 12/860,760 mailed Sep. 27, 2012, 21 pages.

U.S. Final Office Action for U.S. Appl. No. 12/860,760 mailed Dec. 17, 2012, 23 pages.

Notice of Allowance and Fees Due for U.S. Appl. No. 12/860,760 mailed Jun. 24, 2013, 9 pages.

U.S. Office Action for U.S. Appl. No. 13/216,085 mailed Nov. 28, 2012, 27 pages.

U.S. Final Office Action for U.S. Appl. No. 13/216,085 mailed Apr. 3, 2013, 25 pages.

U.S. Office Action for U.S. Appl. No. 13/023,445 mailed Mar. 15, 2013, 29 pages.

Notice of Allowance and Fees Due for U.S. Appl. No. 13/023,445 mailed Aug. 6, 2013, 9 pages.

U.S. Office Action for U.S. Appl. No. 13/088,033 mailed May 22, 2013, 10 pages.

Notice of Allowance and Fees Due for U.S. Appl. No. 13/088,033 mailed Sep. 18, 2013, 13 pages.

U.S. Office Action for U.S. Appl. No. 13/216,085 mailed Sep. 9, 2013, 23 pages.

Notice of Allowance in U.S. Appl. No. 13/756,282, mailed May 12, 2015, 23 pages.

* cited by examiner

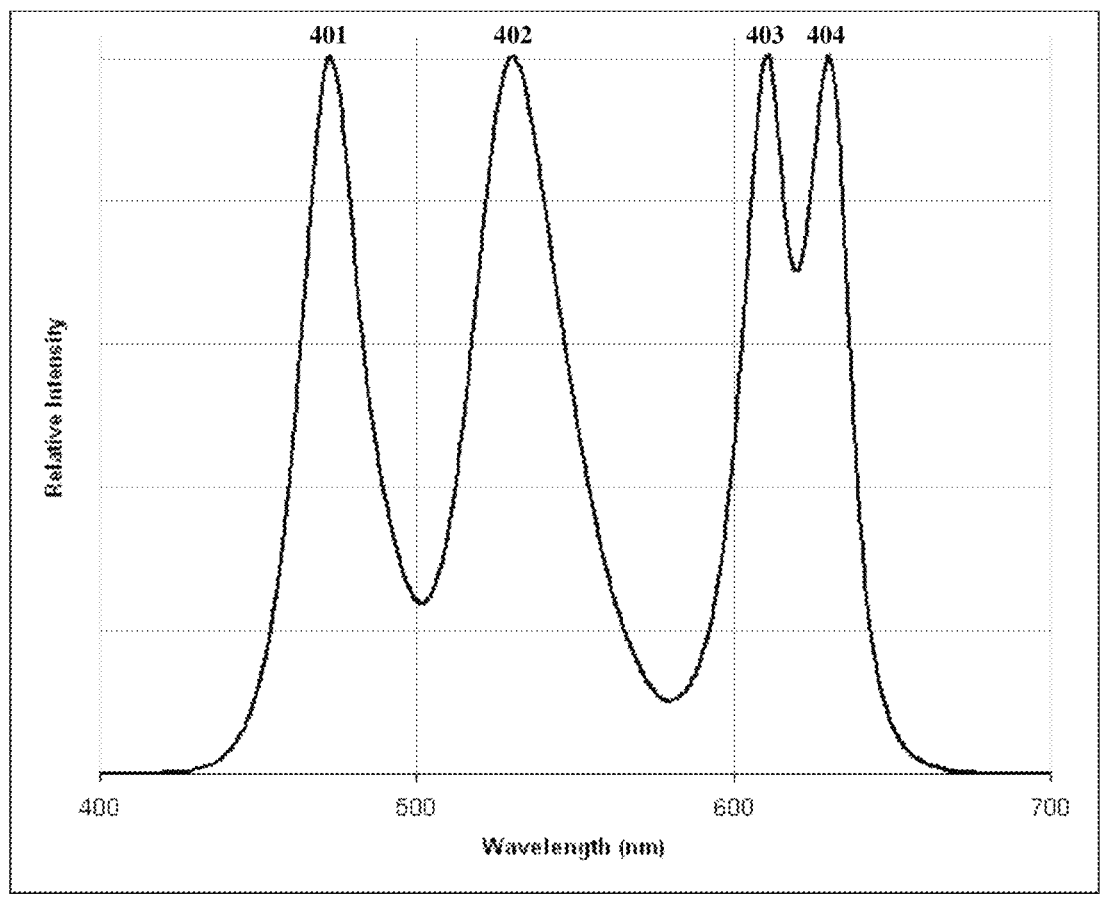
FIG. 4 – PRIOR ART

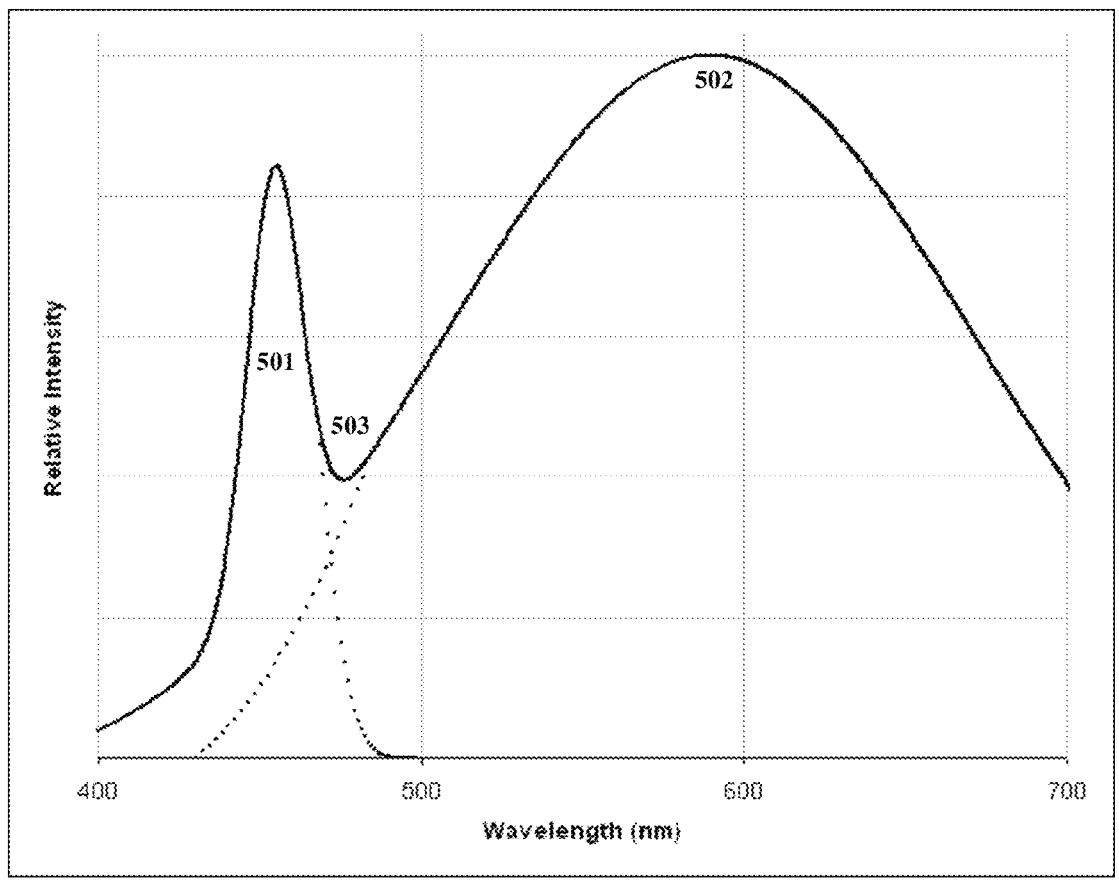
FIG. 5 – PRIOR ART

POLAR CANDELA DISTRIBUTION PLOT

BROAD-SPECTRUM ILLUMINATOR FOR MICROSCOPY APPLICATIONS, USING THE EMISSIONS OF LUMINESCENT MATERIALS

CROSS-REFERENCE TO RELATED APPLICATION

This application claims priority from U.S. Provisional Application No. 61/765,279 filed Feb. 15, 2013, which is hereby incorporated in its entirety by this reference.

BACKGROUND

The present invention relates generally to illumination for microscopy applications, including both fluorescence microscopy and general microscopy applications, and specifically to an illumination apparatus that uses phosphor emissions to provide broad-spectrum white light. By using multiple phosphor types, the illumination apparatus provides a broad-spectrum light output that is highly suitable for exciting the large variety of fluorescent dyes that are used in fluorescence microscopy applications, from a single illuminator. In addition, the illuminating apparatus can provide high-quality white light for brightfield viewing in general microscopy applications, including visible light image capture and photography.

Fluorescence microscopy is popularly used in numerous bio/medical applications since it enables users to label and observe specific structures or molecules. Briefly, fluorescence is a chemical process in which light of a specific wavelength or wavelength range is shined upon a fluorescent molecule, causing electrons from said fluorescent molecule to be excited to a high energy state, in a process known as excitation. These electrons remain briefly in this high energy state, for roughly a nanosecond, before dropping back to a low energy state and emitting light of a longer wavelength. This process is referred to as fluorescent emission, or alternatively as fluorescence.

In a typical fluorescence microscopy application, one or more types of fluorescent materials or molecules (also referred to as fluorescent dyes) are used, along with an illuminator apparatus that provides the exciting wavelength, or wavelengths. Different fluorescent molecules or dyes can be selected to have visually different emission spectra. Since the different fluorescent molecules or dyes that are typically used in fluorescence microscopy applications typically have different excitation wavelengths, they can be selectively excited so long as the bandwidth of the excitation light for one fluorescent molecule or dye does not overlap the excitation wavelengths of other fluorescent molecules or dyes that are being used in the same experiment. This is typically achieved by using specific wavelength-range bandpass filters to create narrow bandwidth excitation light. Broadband excitation light may also be used to simultaneously excite multiple fluorescent dyes. Furthermore, fluorescence is a probabilistic event with low signal levels so an intense light is typically used to increase the chances of the process occurring. Most fluorescence microscopy applications also benefit from having a uniformly intense illuminated field of view or area, ideally such that the size and shape of the illuminated area can be modified. Simultaneously achieving all these criteria has been difficult, but is necessary for current and future applications that require increasing levels of illumination control and consistency.

Traditional prior art fluorescence microscopy illuminators have relied on metal halide arc lamp bulbs such as Xenon or Mercury bulbs, as light sources. The broad wavelength spectrum produced by these lamps, when combined with specific color or bandpass filters, allows for the selection of different illumination or excitation wavelengths. Alternatively, multiple fluorescent dyes, with different excitation and emission wavelengths, may be simultaneously excited. In this type of implementation using metal halide arc lamp bulbs, the speed with which different wavelengths can be selected is limited by the mechanical motion of moving various filters into place. In addition to the sluggishness and unreliability of filter wheels, metal halide arc lamps are also hampered by the limited lifetime of the bulb, typically ~2000 hours. The intensity of the light output declines with bulb use and once exhausted, the user has to undergo a complicated and expensive process of replacing the bulb and subsequently realigning the optics without any guarantee that the illuminator will perform as before. These disadvantages make acquiring consistent results difficult and inconvenient for users who must deal with the variable output of the bulbs, and who must either be trained in optical alignment or call upon professionals when a bulb needs to be replaced. In addition, metal halide arc lamps produce substantial heat, including radiated emissions in the infrared region that can cause heating of the illuminated specimens. This can lead to specimen damage, especially in the case of biological specimens. Similarly, radiated emissions in the UV region may also harm specimens. (In both cases, the use of appropriately designed excitation filters can prevent specimen exposure to damaging wavelengths.)

In recent years, several prior art multiple wavelength illuminators have been developed using different colored LEDs as light sources, that overcome numerous limitations of metal halide arc lamps. Not only do they last longer, with the lifetime of an LED chip being typically rated at well over 10,000 hours, but in addition the power output varies negligibly over that period. Furthermore, the bandwidth of the spectral output of an LED chip is typically narrow (<30 nm) which may eliminate the need for additional bandpass filters. The intensity of the output light can be quickly and accurately controlled electronically by varying the current through the LED chip(s), whereas in metal halide illuminators, the output intensity of the bulb is essentially fixed, and apertures or neutral density filters are used to attenuate the light entering the microscopy.

Prior art LED illuminators for fluorescence microscopy have thus far used up to 5 separate LED modules, each containing one, up to a few chips, for each wavelength. Since the LED chips in these modules have their own individual packaging, the modules are large so that light beams emitted from the modules will need to be combined using optical elements. Although such prior art LED illuminators allow the user the flexibility to swap out modules for new modules with different wavelengths, the additional elements such as lenses, mirrors and heat sinks required for each separate color add complexity, bulk and cost. Furthermore, the long optical paths required to combine the beams from multiple LED chips or modules that are spatially separated, make it difficult to collect and shape already highly divergent light coming from the LED chips. Even when multiple LEDs are packaged or mounted close to each other, the light output of LED chips that are located even a short distance away from the optical axis will be poorly coupled to the objective lens of the microscope.

Another limitation of prior art LED illuminators for fluorescent microscopy is that there is a "dead zone" in the visible light spectrum, where LED chips are either not readily available, or are of very limited optical output. This dead zone is roughly in the portion of the visible light spectrum that lies between green and amber (or orange), in the approximate wavelength range of 540-595 nm. Unfortunately, several popular fluorescent dyes require excitation light that is in this dead zone.

These practical issues have limited the application of such illuminators in fluorescence microscopy, which in general requires light that is both intense and spatially uniform, across the full range of wavelengths that are required for the excitation of popular fluorescent dyes.

Although the narrow spectral bandwidth (typically <30 nm) of individual LEDs can be an advantage in some fluorescent microscopy applications, bandpass excitation filters may still be needed, in order to more closely match the excitation wavelength requirements of the dye(s) being used. If excitation filter(s) are being used anyway, then the narrow spectral bandwidth of LEDs can become a disadvantage, in that the LED wavelengths being used must be selected to match the types of dyes being used. For this reason, it is desirable to have a broad-spectrum illumination apparatus that provides the lifetime, reliability, and other advantages of an LED illumination apparatus.

In order for LED illuminators and light engines to act as a satisfactory replacement for illuminators used in general microscopy applications, such as brightfield illuminators, it is desirable and even necessary to produce white light with characteristics that are similar to the light produced from an incandescent bulb, or in some cases, to accurately replicate the light provided by natural sunlight. This is especially important for microscopy applications that demand high quality light with well-controlled parameters. This is true for human eye viewing, as well as microscope photography and imaging. In a general sense, this means that the LED illuminator or light engine should have a broad spectral response or characteristic that mimics the spectral response of an incandescent bulb, and/or natural sunlight.

SUMMARY OF THE INVENTION

One embodiment of the invention is directed to a broad-spectrum, multiple wavelength illuminator for providing light along an optical axis, comprising a luminescent body, and a plurality of semiconductor chips emitting light within one or more wavelength ranges towards the luminescent body, causing the luminescent body to emit light of one or more wavelength ranges, the plurality of semiconductor chips spaced apart from the luminescent body. An optical element adjacent to the luminescent body is used to collect light emitted by the luminescent body. An optical device is used to collect and direct light emitted by the luminescent body and collected by the optical element along the optical axis. Preferably and as an option, an aperture located in the optical axis between the optical element and the optical device passes the light emitted by the luminescent body along the optical axis, wherein light collected by the optical element and the optical device and passed by the aperture forms a beam of light illuminating a target.

Another embodiment of the invention is directed to a method for providing light along an optical axis, comprising causing a plurality of semiconductor chips to emit light within different wavelength ranges towards a luminescent body spaced apart from the plurality of semiconductor chips, causing the luminescent body to emit light, collecting light emitted by the luminescent body, passing the light collected from the luminescent body through an aperture to form a beam along the optical axis; and collimating the beam and directing the collimated beam along the optical axis to a target.

Yet another embodiment of the invention is directed to a broad-spectrum, multiple wavelength LED array illuminator for providing light along an optical axis, comprising a substrate and at least one array of multiple LED chips without individual packaging supported by the substrate, wherein the LED chips are distributed laterally with respect to the axis over an area, the LED chips having light emitting surfaces for emitting light in directions transverse to the area. A luminescent layer on at least some of the LED chips emits light in the yellow region of the visible spectrum in response to light emitted by the at least some of the LED chips, and may also emit light in other regions of the visible spectrum. An optical element adjacent to the light emitting surfaces of the LED chips in the at least one array collects and directs light emitted by the LED chips of the at least one array and by the luminescent layer along the axis towards a target, wherein the light received by the target from the optical element is of substantially uniform intensity across a broad spectrum.

BRIEF DESCRIPTION OF THE DRAWINGS

FIG. 4 is a representation of the prior art, showing the spectral profile of an LED-based fluorescence microscopy illuminator providing four specific wavelengths of excitation light.

FIG. 5 is a representation of the prior art, showing the spectral profiles of an LED light source that is exciting emissions from a luminescent material, such as a phosphor material.

DETAILED DESCRIPTION OF THE PREFERRED EMBODIMENTS

Figure 1:
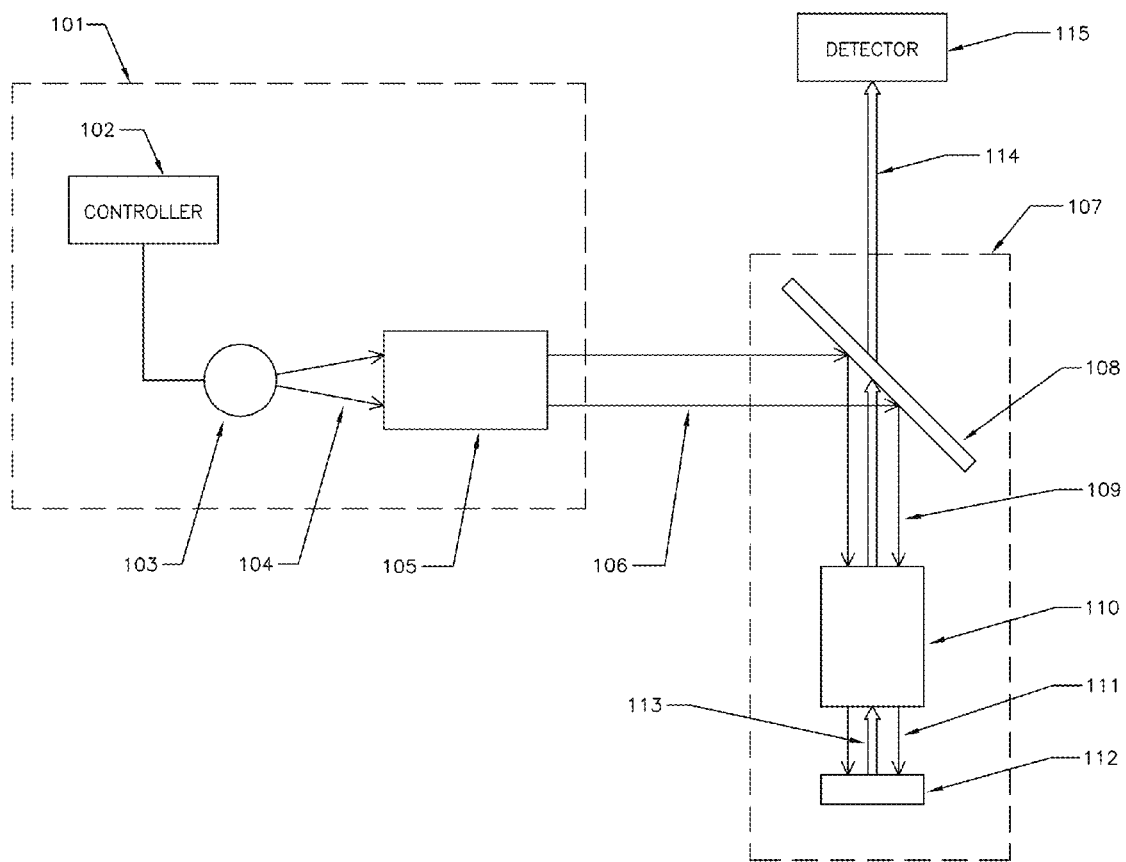
FIG. 1 is a representation of the prior art in fluorescence microscopy illumination, showing the major elements of a typical system.

FIG. 1 is a representation of the prior art in fluorescence microscopy illumination, showing the major elements of a typical system, as described in U.S. Pat. No. 6,154,282 (Lilge et al., issued Nov. 28, 2000). An excitation illuminator (101) is made up of a controller (102), a light source or light engine (103) that provides the required wavelength or wavelengths of excitation light (104), and an optical system (105) that is designed to provide collimated light, or nearly collimated light (106), into an optical port of a microscope.

Light entering the microcope (107) is reflected by a wavelength-selective dichroic mirror (108). This reflected excitation light (109) is further shaped by optics within the microscope (110), including the objective lens of the microscope, so that the excitation light is directed (111) onto the stage (112) of the microscope, which holds or contains the specimen that has been dyed with one or more fluorescent dyes.

The fluorescent dyes in the specimen absorb energy from the excitation light source, and emit higher wavelength light (113). These emissions pass back through the microscope optics (110), including the objective lens, and also pass through the dichroic mirror (108). The dichroic mirror has been selected to have a cut-off wavelength that is higher than the wavelength(s) of the excitation light source, but lower than the emissions wavelength(s) of the dyes that are used on the specimen. Assuming that a properly-specified dichroic mirror is installed in the microscope, the emissions light (114) from the specimen will pass through to a detector (115), which may be an eyepiece for direct viewing, or a camera for capturing images. Note that any stray excitation light that is reflected from the specimen will be blocked by the dichroic mirror, and reflected back towards the excitation light source or illuminator.

Figure 2:
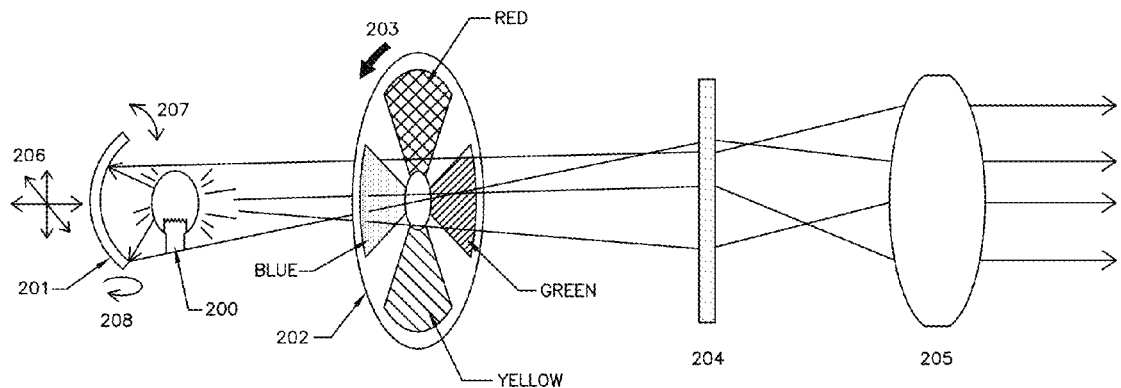
FIG. 2 is a representation of a prior art illuminator for fluorescence microscopy, using an incandescent bulb as a broad-spectrum light source.

FIG. 2 is a representation of a prior art illuminator for fluorescence microscopy, using a metal halide arc lamp (200) as the light source. Since the metal halide light source emits broadband light, a variety of color filters is used to provide excitation light with a controlled spectral profile, or passband. A typical carousel filter wheel is shown in FIG. 2 as item 202, with its direction of rotation indicated by item 203. Since the lamp filament in the metal halide arc lamp bulb (200) which emits light is of relatively large size, and therefore acts as an extended or non-ideal (i.e., not a point) light source, significant optical treatment must be done to make the illumination area uniform. This typically involves either using dispersive diffusers (204) or field stops and apertures (not shown) for Koehler illumination, for instance, both of which reduce the optical power of the excitation light. A lens (205) is used to provide a collimated, or nearly-collimated beam, into the optical port of the microscope.

Metal halide arc lamps have several significant disadvantages, including the short lifetime of the bulbs, and the fact that over the lifetime of a bulb, its intensity continually decays. Most metal halide lamps require a warm-up period of around 30 minutes for their output to stabilize, which can be inconvenient for users with time sensitive samples. With rated lifetimes of anywhere from a few hundred hours, to as long as perhaps 2,000 hours, metal halide bulbs must often be replaced several times a year which is not only inconvenient and expensive, but difficult and often requires the hiring of professionals. Alignment typically requires adjusting the multiple degrees of freedom of a reflector surrounding the bulb (FIG. 2, item 201, with the multiple adjustments depicted by arrows 206, 207, and 208) which is not necessarily a tedious process, but often requires training and is hence inaccessible to many users unfamiliar with optics.

Prior art multiple wavelength LED illuminators have overcome some of the limitations of metal halide ones but have been complicated, requiring many optical elements, and hence costly to manufacture. LEDs emit light with narrow bandwidth (typically on the order of 20-30 nm for a specific LED chip), which can be an advantage for many fluorescence microscopy applications. Unlike metal halide bulbs, LED chips have lifetimes rated at well over 10,000 hours and do not require a warm up period before reaching full output. The ability to have multiple wavelengths is achieved by using LED chips that emit different colors. Each LED chip resembles a point source more than metal halide bulbs do and therefore it is usually easier to homogenize the illumination intensity distribution.

Figure 3:
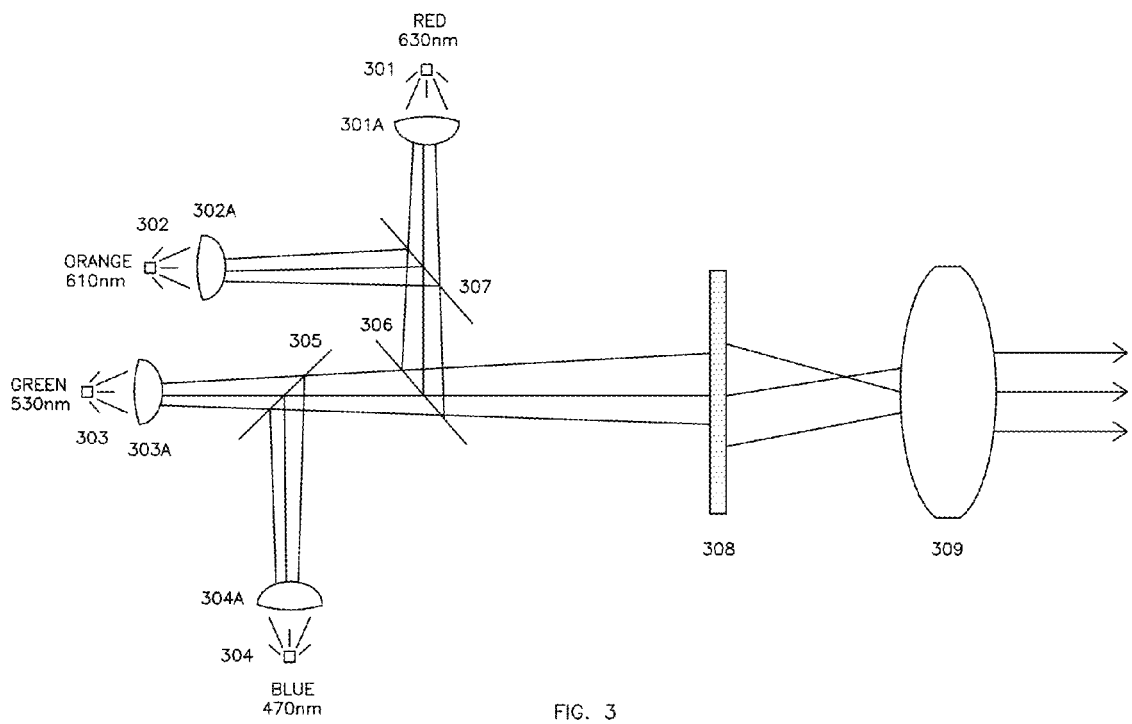
FIG. 3 is a representation of a prior art illuminator for fluorescence microscopy, using multiple wavelengths of LEDs as the light sources.

In the prior art embodiment shown in FIG. 3, each wavelength comes from separate LED "modules" (FIG. 3, items 301-304). Since prior art LEDs are typically packaged as separate, individual chips, or as small cells with a few chips, the LED modules are relatively large, so that each module will need to have its own set of collecting and collimating optics (items 301A-304A), whose light paths are then combined using dichroic mirrors (items 305-307). Having separate modules, however, requires long optical paths. In order to collect the maximum amount of light, this prior art embodiment requires large lenses with large numerical apertures that are both costly and bulky. The maximum number of LED wavelengths that can be equipped at any one time is also limited by the cost and complexity of the beam-combining optics.

FIG. 4 shows a spectral plot of an embodiment of the prior art in multiple-wavelength LED illuminators for fluorescence microscopy. In this embodiment, which is similar in structure and function to the prior art embodiment shown in FIG. 3, the four excitation wavelengths being provided have peaks at approximately 470 nm (in the blue region of the visible light spectrum, shown as item 401), 530 nm (green, item 402), 610 nm (orange, item 403), and 630 nm (red, item 404). The specific peak wavelengths would be chosen to coincide with the desired excitation wavelength ranges for four different fluorescent dyes. The excitation light from the four LED wavelengths is narrowband, and so there must be a close match between the LED wavelengths and the excitation requirements of the fluorescent dyes. Despite the narrow spectral profile of each LED type, it may still be necessary to use narrow passband excitation filters, to further limit or shape the spectral profiles of the four excitation wavelengths.

One disadvantage of using LEDs as the excitation light source(s) is that there is a well-known "gap" or "dead zone"

in the yellow portion of the visible light spectrum. Above an approximate wavelength of 595 nm, high brightness and high-efficiency amber, orange, red and infra-red LEDs are readily available (typically based on Gallium-Arsenide, or GaAs materials). Below an approximate wavelength of 540 nm, high brightness and high efficiency green, blue, indigo, violet and even UV LEDs are readily available (typically based on Indium-Gallium-Nitride, or InGaN materials). However, between approximately 540 nm and 595 nm, it is difficult or even impossible to obtain LEDs with good brightness and/or quantum efficiency. This "dead zone" between 540 nm and 595 nm can be seen visually in FIG. 4. It is particularly unfortunate for fluorescence microscopy, in that several popular fluorescent dyes require excitation light in the LED "dead zone" wavelength range. For reference, the table below lists several popular fluorescent dyes, along with their preferred excitation wavelength, and their peak emission wavelength:

| Common Dye Name | Excitation Wavelength (nm) | Peak Emission Wavelength (nm) |
|---|---|---|
| DAPI | 345 | 455 |
| ECFP | 434 | 477 |
| FITC | 490 | 520 |
| GFP (EGFP) | 488 | 510 |
| EYFP | 515 | 527 |
| Cy3 | 552 | 570 |
| MitoTracker Orange | 551 | 576 |
| Rhodamine Red | 560 | 580 |
| TAMRA | 565 | 580 |
| MitiTracker Red | 578 | 599 |
| Texas Red | 591 | 613 |
| mCherry | 587 | 615 |
| Cy5 | 648 | 666 |

A common method for providing an LED light source with a relatively broad spectral response (to provide white light, for example), is to use one or more blue LED chips that have been coated with phosphors, or other luminescent material. Excitation of the phosphor material by the blue LEDs induces Stokes shift in the emission of light from the phosphor, resulting in an emission wavelength range that is at higher wavelengths than the excitation wavelength. The Stokes shift can range from a few tens of nanometers, to as much as 200 nm or more. In LED illuminators, the excitation wavelength for the phosphors or other luminescent material is typically in the range of 410 nm to 490 nm (indigo to blue). Depending on the luminescent material used, the major emission wavelength range may be in the green, yellow, or red portions of the visible light spectrum. Such phosphor formulations are commercially available, and are designed to absorb energy at particular lower wavelengths (such as are emitted by blue LEDs), and to emit light at higher wavelengths. The emissions from said phosphors have a much wider spectral bandwidth, typically with FWHM values of 50-120 nm, versus only 20-30 nm for typical LEDs. Commercially available phosphors are typically available in the form of small particles or powders, with typical materials being silicates, aluminates, garnets, and nitrides, with various attributes of emission wavelength range, efficiency, lifetime, etc. The phosphor material(s) are typically mixed into some form of silicone gel or epoxy, and then applied to the top surface of the LED chip(s). Quantum dots may also be used as the luminescent material, as described below.

FIG. 5 shows a spectral plot of a prior art LED illuminator, showing the direct spectral output from blue LEDs (501), as well as the broader spectral output from the applied phosphor material(s), primarily in the yellow region of the spectrum (502). With appropriately chosen phosphor materials and proper application of the phosphor materials to the LEDs, this prior art light source can be designed to provide white light of moderately high quality, with a variety of correlated color temperatures (CCT), and with an overall spectral profile as depicted by item 503.

According to one embodiment of the invention, a compact illuminating apparatus comprises one or more light sources that are used to stimulate or excite light emission from one or more luminescent materials, including materials such as phosphors and quantum dots. In subsequent discussion, any use of the terms "phosphors" or "phosphor materials" can be assumed to also include the use of other luminescent materials, such as quantum dots. The light that is emitted by the luminescent material is then directed to the object(s) to be illuminated, through the use of optical elements such as reflectors, lenses, and/or diffusers, etc. Note that the object(s) to be illuminated may include objects that have been treated with fluorescent dyes, as in fluorescent microscopy applications. In this case, the light being emitted by the phosphors or other luminescent material of the present invention, will in turn excite emissions from the fluorescent dyes that have been applied to the object(s) being illuminated.

The phosphors or other luminescent materials may be deposited as a layer directly onto the excitation light source, typically by incorporating the phosphor materials into a silicone or similar gel. In this embodiment of the present invention, the excitation light that is not absorbed by the phosphor will be combined with the emissions from the phosphors, so that the combined light output is directed to the object(s) to be illuminated. The phosphors or other luminescent materials may be deposited as a layer on some or all of the excitation light source, such as some or all of a plurality of LEDs.

It is also possible to excite the phosphors or other luminescent materials from one or more external light sources that are not directly contacting the phosphor materials. The external excitation source(s) may comprise one or multiple LEDs, although other types of excitation light sources may also be used, such as semiconductor lasers (including vertical-cavity semiconductor lasers, or VCSELs, Organic LEDs (OLEDs), or electroluminescence sources. The external excitation light source(s) should be compact, with stable light emission, and low heat generation. In this embodiment of the present invention, light from the external excitation source(s) is used solely for excitation of the phosphors or other luminescent materials that are contained within the illuminator apparatus, and does not directly contribute or add to the illumination of the intended object(s) through the microscope optics. Therefore, when this embodiment is being used for fluorescence microscopy applications, the emissions from the phosphors or other luminescent materials that are contained within the illuminator apparatus act as the excitation light source for any fluorescent dyes that are applied to the samples or specimens that are being viewed through the microscope. However, in some embodiments, a portion of the excitation light from the external excitation source(s) may be combined with the emissions from the phosphors or other luminescent materials, such that the combined light is used to illuminate the intended object(s) through the microscope optics.

Multiple types of phosphors or other luminescent materials, with different emissions spectra, may be combined, in order to achieve a very broad overall spectral profile. The area or volume of phosphor, or other luminescent material, is kept small, so that the etendue of the emitted light is minimized. Depending on the brand and model of microscope, the achieving of good coupling of light into the microscope optics may require that the light emitting area of the phosphors is just a few mm across. By focusing excitation light from multiple excitation sources, onto a small area or volume of phosphors or other luminescent material, the etendue of the overall light source may be significantly smaller than the combined, effective etendue of the excitation sources. This provides significant advantages in fluorescence microscopy applications, where minimal etendue is essential for efficient coupling of light into the optics of the microscope. The broad-spectrum emissions from the multiple phosphor types or other luminescent materials also provide high quality white light, for brightfield illumination and other general microscopy applications. The ability to mix multiple phosphor types or other luminescent materials into a silicone gel provides for a broadband emissions spectrum that is spatially uniform, with high color or hue uniformity.

Optical elements including reflectors, lenses, and/or diffusers may be used to further shape the beam, and to further improve the homogeneity and uniformity of the beam. Separate lenses and/or reflector elements may also be used with external excitation LEDs or other excitation light sources, to focus the excitation light onto the phosphors or other luminescent material.

As fluorescence microscopy becomes increasingly popular in bio/medical applications the demand for powerful, reliable, and affordable illumination sources has increased as well. Fluorescence microscopy has evolved as a tool not only for viewing specific structures, but for quantitatively measuring their distribution and dynamics as well. These quantitative measurements benefit from illumination sources that are stable over long periods of time and will last at least the lifetime of the experiment or project. To increase time resolution, faster exposure times are being used which typically requires a stronger excitation signal and hence intense illumination. Furthermore, to simplify background calibrations, the illumination area, which can be larger than the microscope's field of view, should be uniform in intensity. Simultaneously achieving all the above features of an ideal fluorescence illuminator has been thus far either exceedingly difficult and/or expensive. The present invention overcomes several of the disadvantages of prior art fluorescence microscopy illuminators and satisfies the needs for many fluorescence microscopy applications.

The present invention seeks to provide a broad spectrum light source or illumination apparatus, that provides all of the wavelengths and/or wavelength ranges that are needed to excite the broad range of fluorescent dyes used in fluorescence microscopy. In order to provide the long lifetime, reliability, and other advantages of LED illuminators, the present invention uses LEDs and other long lifetime, reliable light sources to excite emissions from multiple luminescent materials, such that their combined light output meets the excitation requirements of said fluorescent dyes. In addition, the broad spectrum illumination apparatus can be designed to produce high-quality white light for brightfield illumination applications in microscopy. In one embodiment of the present invention, these objectives are achieved by using one or multiple wavelengths of blue LEDs, all of which are coated with multiple types of phosphors or other luminescent materials, having differing spectral profiles for their emissions. Further, by having independent control of the drive current for different subsets of the LED chips and their respective phosphor types, the combined spectral profile of the illumination apparatus can be easily adjusted or varied.

Figure 6A:
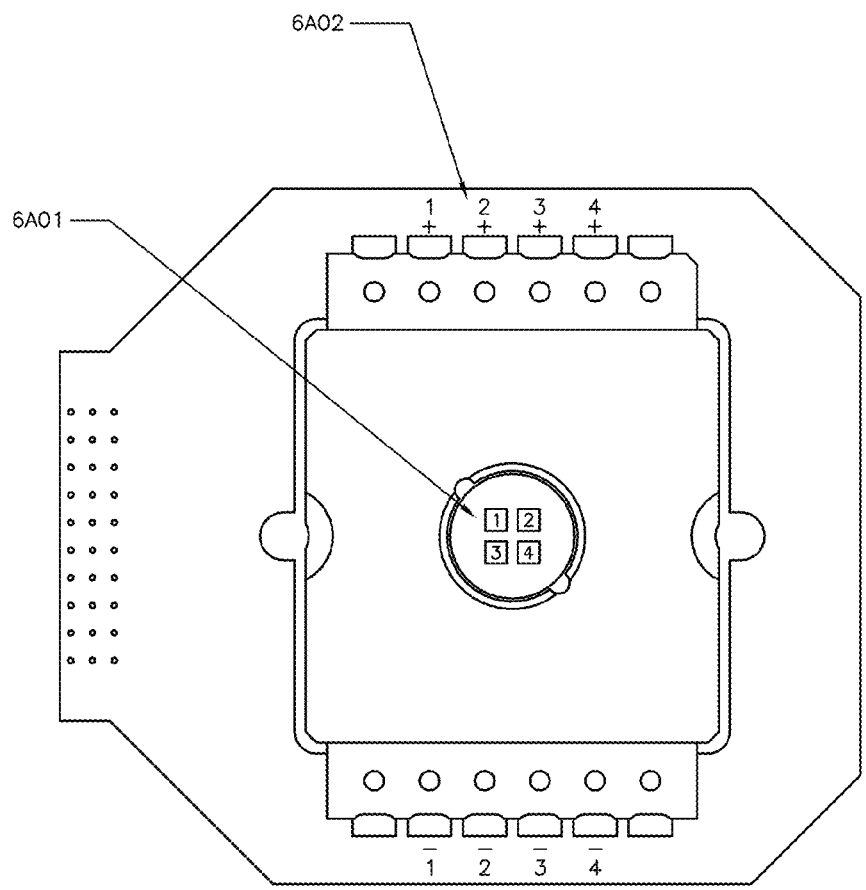
FIGS. 6A and 6B show two views of one embodiment of an LED array of the present invention, showing the use of multiple LED chips with multiple phosphor types.
Figure 6B:
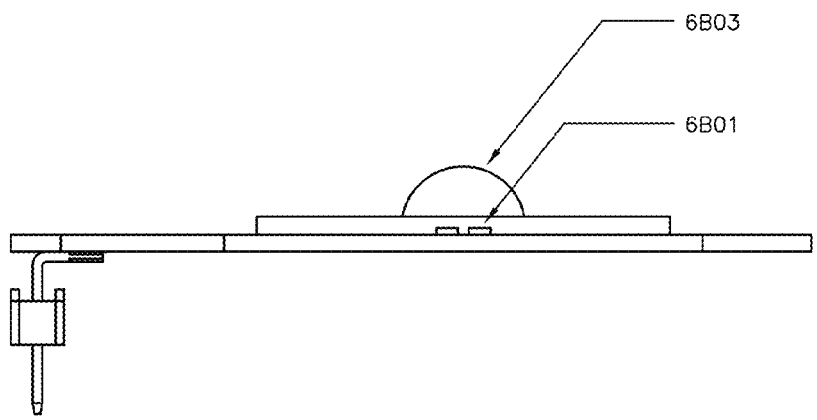

FIGS. 6A and 6B show front and side views, respectively, of one embodiment of an LED array of the present invention. The LED array typically comprises a multiplicity of individual LED chips (6A01 and 6B01). The LED array embodiment depicted in FIGS. 6A and 6B contains four LED chips, in order to keep the light emitting area and etendue of the illuminator as small as possible, although in other embodiments the number of LED chips may be as small as one, or in excess of 100. The individual LED chips of the embodiment shown in FIGS. 6A and 6B are approximately 1 mm×1 mm in size. However, LED chips of other dimensions may also be used, and the diameter of the light-emitting area is therefore a function of the number of LED chips, the individual chip dimensions, and the spacing between LED chips. In FIG. 6A, the LED chips are shown as element 6A01, with each small square representing an individual LED chip. The LED chips may occupy an area on the substrate of about 2-15 mm in dimensions. The diameter of the light-emitting area of the array is approximately 2-15 mm, depending on the number of LED chips in the array, as well as the individual chip size and spacing, thereby allowing the LED array to function as an "extended point source". For good coupling of light into the microscope optics, it is preferable for the LED array to have a small light-emitting area of 2-10 mm, or even 2-4 mm. Note that the single lens that is placed over the light-emitting area of the LED array (6B03) may have a diameter that is slightly larger than the actual light-emitting area, such as a diameter of about 3-20 mm.

The LED chips within each array are connected electrically into multiple channels, each channel consisting of at least one LED chip, or a series string of multiple LED chips. An LED string or channel is controlled as a single entity, with all LED chips within the series string having an identical electrical current passing through them, and therefore each chip within a string will produce light of similar brightness. In the embodiment shown in FIGS. 6A and 6B, each of the four individual LEDs is controlled as a separate channel. Separate electrical connections (6A02) are provided for each LED channel or string within the array, either in the form of electrical pins, or as electrical pads, as shown in the figure, so that the relative brightness of the different strings can be controlled and varied independently. The embodiment shown in FIGS. 6A and 6B comprises four channels of LED chips, with the channel number shown within each LED chip (6A01), and also adjacent to the electrical connections (6A02). Note that the number of channels may vary, and is limited by the number of LED chips, the number of available electrical connections, and by constraints on the routing of electrical paths within the array. Also, channels may be electrically connected to each other, external to the array, if fewer separately-controllable channels are required. For example, although the embodiment shown in FIGS. 6A and 6B comprises four channels of LED chips, the driver circuit for the embodiment might comprise one, two, three, or four driver circuits, each of which is driving one, or multiple LED channels or chips. Typically, if multiple LED channels are to be driven by a single driver circuit, they would be connected in series, such that the drive current in the combined channel would be constant. The LED array shown in FIGS. 6A and 6B also incorporates one or more internally-mounted thermistor chips, which are brought out to some of the unlabeled electrical connections, for the purposes of monitoring array temperature, which may be incorporated into the overall thermal management scheme of the illuminator.

Thermal management is a key element of the design of the present invention, in order to extract the heat that is generated by the potentially large number of LED chips that are packaged closely together in the LED array. The LED array incorporates a metal circuit board (MCB) which provides for the routing of conductive traces to each of the LED strings, while at the same time providing electrical isolation between LED strings. The MCB also provides for high thermal conductivity, to extract heat from the densely-packed LED chips. The MCB LED array substrate, having the thermal conductivity of metal, conducts the heat from the LEDs to the base of the MCB substrate, which is mounted onto a heat spreader or heat sink. The MCB of the present invention is described in more detail in U.S. Pat. No. 8,044,427, issued on Oct. 25, 2011, entitled "LIGHT EMITTING DIODE SUBMOUNT WITH HIGH THERMAL CONDUCTIVITY FOR HIGH POWER OPERATION".

In most embodiments of the present invention, the one or multiple LEDs within a channel or string would be of similar or identical wavelengths. However, different strings might contain LEDs of widely-varying wavelengths. In one embodiment of the LED array, some strings would consist of different wavelengths of blue, indigo, or violet light. Similarly, an individual LED string or channel might use just a single phosphor type (or other luminescent material), or it might use multiple phosphor types. Note that in all cases, all of the LED chips of the array are coated by one or more phosphor types, with different individual LED chips, even adjacent chips, having potentially different phosphor types coated onto them. The application process for applying phosphor materials to the LED chips allows for a differing, or even unique phosphor formulation, to be applied at each one of the multiple LED chip sites. The phosphor formulation on any given chip may consist of a single type of phosphor material, mixed into a silicone gel material, or a blend of multiple types of phosphor materials mixed into the gel, for an even broader spectrum. By separately controlling the electrical current flowing through different LED strings, the relative proportions of light of different spectral characteristics can be varied. Within a particular string, it is still possible to use individual LED chips of multiple wavelengths, although the intensity of the light emission of the LED chips within a string will be of the same order of magnitude. In one embodiment of the present invention, multiple wavelength ranges of blue, and indigo light (for example, LED chips with peak wavelengths at approximately 430 nm and 455 nm) could be used, in order to achieve broader coverage of the blue portion of the spectrum, as well as optimal excitation of specific phosphor types. Similarly, multiple wavelength ranges of phosphors, such as predominantly green, yellow, and red-emitting phosphors could be used either within a string, or in multiple strings, in order to achieve broader coverage of the green, yellow and red portions of the spectrum. If other luminescent materials are used, such as quantum dots, then the emissions spectra of the multiple luminescent material types may include predominantly blue light, in addition to predominantly green, yellow, and red light.

Figure 7A:
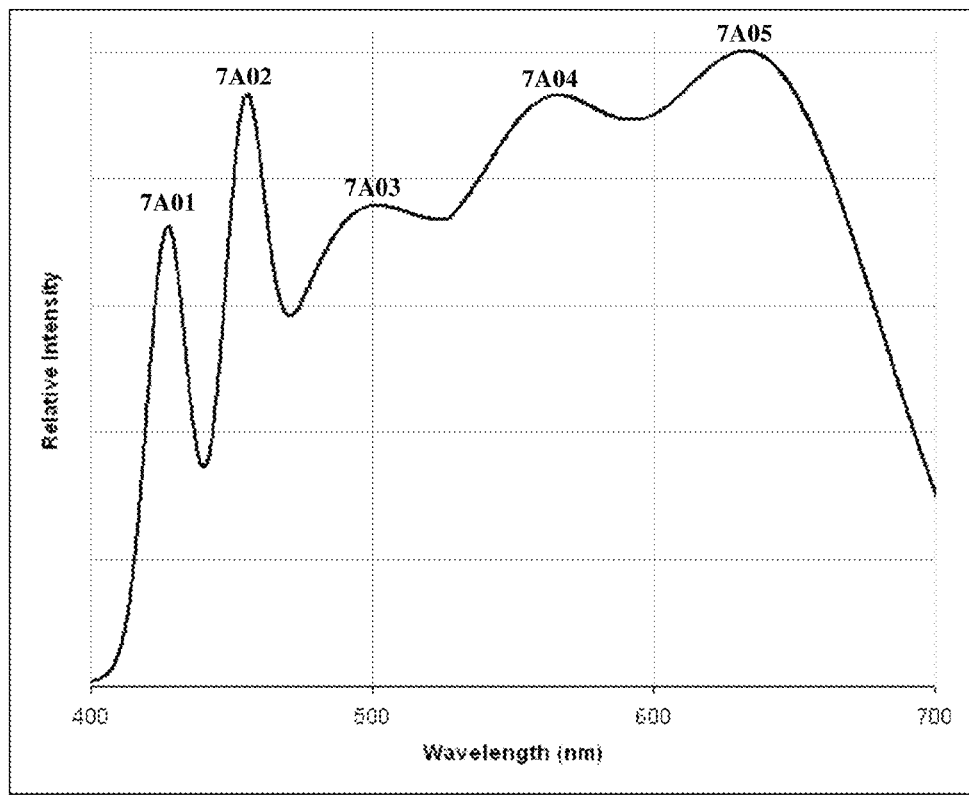
FIGS. 7A and 7B are representations of the spectral profiles of two embodiments of the present invention.

FIG. 7A shows a spectral plot of one embodiment of the present invention, based on the LED array embodiment depicted in FIGS. 6A and 6B. The LED array of this embodiment comprises two wavelengths of generally blue LEDs, with spectral peaks at approximately 430 nm (7A01) and 455 nm (7A02), respectively. The LED chips of this embodiment are coated with three types of phosphors, that absorb energy from either or both of the blue LED chip types, and emit broad spectrum light with emissions that are roughly in the green (7A03), yellow (7A04), and red (7A05) portions of the visible spectrum. It should be noted that all of the LED chips of this embodiment are coated with at least one of the phosphor types. Applying a mixture of phosphor types onto a given LED chip, or set of LED chips, will result in a broader spectral output from those particular chip location(s), potentially improving the color and hue uniformity within the field of view of the illuminator. As noted previously, the application process for the phosphors allows differing phosphor types or mixtures of phosphor types to be applied at differing LED chip sites, even to the extreme of having a unique phosphor mixture for every LED chip. Although the embodiment depicted in FIG. 7A uses two wavelengths of generally blue LEDs, other embodiments might use just a single wavelength of generally blue LED, or more than two wavelengths. Similarly, the number of phosphor types may be less than, or more than, three.

Figure 7B:
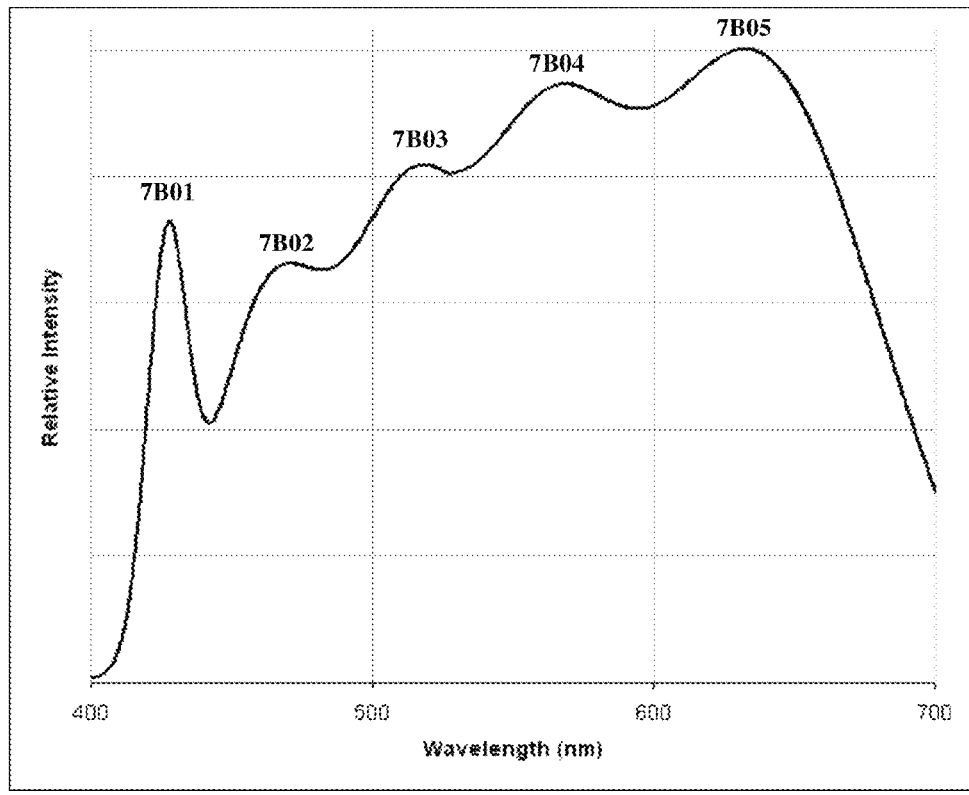

The embodiment shown in FIG. 7B uses a single wavelength of LED chip, with a peak wavelength that is close to 430 nm (7B01). In this embodiment, a luminescent material is used that has significant emissions in the blue region of the visible light spectrum (7B02), in addition to the luminescent materials with emissions in the green (7B03), yellow (7B04), and red (7B05) regions of the visible light spectrum.

As shown in both FIGS. 7A and 7B, the combined spectral output of the blue LED wavelength(s), and the multiple phosphor types (or other luminescent materials), results in a spectral plot with both good spectral fill (i.e., without deep gaps in the spectrum), and also the avoidance of spectral "hot spots", due to excessive output at specific wavelengths, thus closely approximating the output of a broadband light source, such as a metal halide or other incandescent bulb. The fact that all of the LED chips of this embodiment are coated in phosphors, or other luminescent materials, significantly reduces the potentially excessive light output at specific narrow wavelength ranges, that would result from having uncoated LED chips. Also, the potential use of multiple wavelengths of blue LED chips (all of which serve to excite emissions from all of the phosphor types used) also serves to avoid excess light output at specific narrow wavelength ranges, in comparison to simply using a single wavelength of blue LED chip.

Some embodiments of the present invention shown in FIGS. 6A and 6B may require the application of different phosphors or other luminescent materials over the tops of individual LED chips, which are spaced tightly together in an LED array. The phosphor or other luminescent material (either of a single wavelength range or type, or in some embodiments multiple types mixed together) is mixed into a silicone gel material, which is dispensed as a viscous liquid, and then cured to become solid. The silicone gel is of high viscosity, and the dispensed quantity must be well controlled, so that each LED chip is fully covered by the silicone gel with its intended phosphor type(s), without spreading to cover adjacent LED chips, since these adjacent LED chips may require the application of a different phosphor type. Commercially available silicone gels for LED packaging applications are designed to be optically transparent throughout the visible light range of wavelengths, extending down to the UV range. They are also designed to have a well controlled index of refraction, for good light extraction from the surface of the LEDs.

One disadvantage of the embodiment of the present invention shown in FIGS. 6A and 6B is that the light-emitting area of the LED array increases in proportion to the number of LED chips in the array. Due to the etendue of larger LED arrays, the coupling efficiency of the light output of the array into the optics of a microscope will decrease as the number of LED chips, and therefore the light-emitting area of the LED array, increases. This is especially true for fluorescence microscopy illuminators, in which the excitation light must pass through a long optical path, including the objective lens of the microscope, before it reaches the dyed samples or specimens that are being illuminated. In practice, most of the useful excitation light comes from the central region of the LED array, from just a few LED chips. Put another way, the useful light emitting area of the LED array may be only 2-4 mm in diameter. For fluorescence microscopy applications, LED arrays that are larger than four or perhaps nine LED chips (assuming typical LED chips that are one mm across) will provide little or no additional excitation light.

Figure 8:
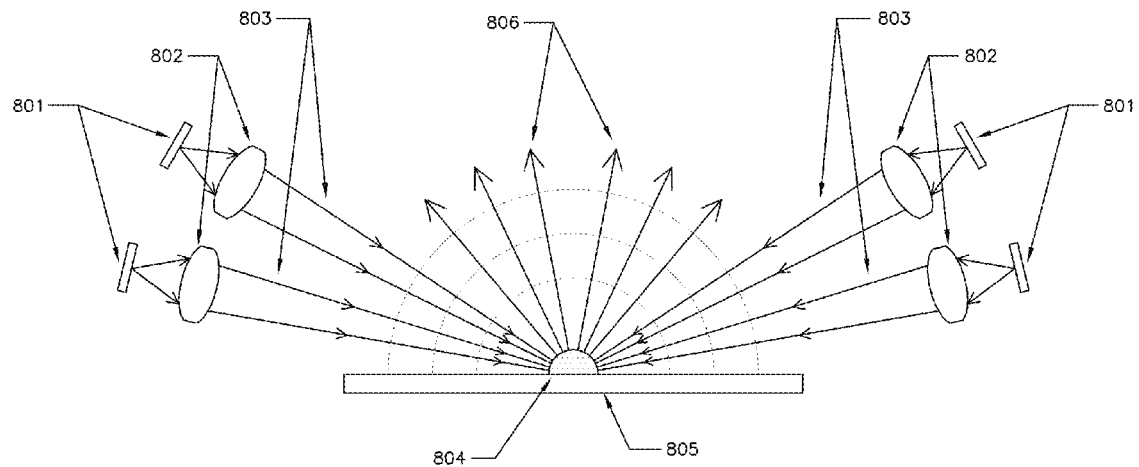
FIG. 8 shows another embodiment of the present invention, in which the LED excitation light sources are separated in space from the light-emitting phosphors or other luminescent material.

Another embodiment of the present invention addresses this problem by physically separating the LED chips that are used to excite phosphor emissions, from the phosphors or other luminescent materials, whose emissions are used to provide the actual excitation light for the fluorescent dyes used on the samples or specimens. This embodiment is represented in FIG. 8. In this embodiment of the present invention, a "blob" of silicone gel (804) containing multiple phosphors (or other luminescent materials) is placed on a substrate (805). Emissions from this blob of phosphors provide the excitation light (806) that is directed into the optics of the microscope, thereby exciting the fluorescent dyes used on the specimen(s).

In order to excite emissions from the blob of phosphors or other luminescent materials (804), multiple blue, indigo, and/or violet LED chips, or small arrays of LED chips (801) are arranged at a moderate distance from the blob of phosphors. Light from these multiple LED chips or small arrays of LED chips is focused by lenses (802), so that the focused light (803) is aimed at the blob of phosphors (804). Note that the multiple LED chips or small arrays of LED chips are located far enough away from the phosphor blob so that they are not blocking the path of the light that is emitted by the phosphor blob. In this way, the combined light output of the multiple LED chips or small arrays of LED chips is directed and concentrated onto a small blob of phosphors, providing excitation of the phosphors (or other luminescent materials) that is equivalent to what would be provided by a much larger individual LED array.

In order to achieve good coupling of light energy from the LED chips or small LED arrays into the blob of phosphors, the cross-sectional size of the blob of phosphors would typically be somewhat larger than the light emitting area of each individual LED chip or small LED array. However, the cross-sectional size of the blob of phosphors can still be significantly smaller than the combined light emitting area of the multiple LED chips or small LED arrays. In this way, the etendue of the blob of phosphors is kept small, so that the coupling of emissions from the phosphor blob into the optics of the microscope is greatly improved.

Depending on the design and orientation of the LED chips or small LED arrays (801), the lenses (802), and the substrate (805), very little of the LED light output, and perhaps none of the LED light output, will couple into the microscope optics. In this case, the blend of phosphors or other luminescent materials should include phosphors or other luminescent materials with emissions that are in the blue range of visible light, and not just in the green, yellow, and/or red ranges of visible light. However, if the substrate (805) is configured as a reflector of appropriate shape, it may be possible for a portion of the light from the LED chips or small LED arrays (801) to be reflected toward or into the microscope optics, in combination with the emissions from the blob of phosphors. The blob of phosphors will ordinarily contain multiple types of phosphors or other luminescent materials, in order to provide broad spectrum light, comprising all of the desired excitation wavelengths for a broad range of fluorescent dyes. In one embodiment the multiple types of phosphors or other luminescent materials is uniformly mixed or distributed within the blob. In other embodiments, the blob consists of multiple "sub-blobs" or regions of the blob, such that each sub-blob or region of the blob contains a different phosphor or mix of phosphors (or other luminescent materials.) The broad spectrum light emitted by these embodiments of the present invention also provides high quality white light for brightfield microscopy applications. The quantity of phosphors or other luminescent material within the blob may also be quite high, in order to achieve a high intensity of light output, from a small effective light-emitting area.

In addition to using one or multiple LEDs or LED arrays as the source(s) of excitation energy for the remotely-located blob of phosphors or other luminescent materials, it is within the scope of the present invention to use other sources of excitation energy, including, but not limited to, solid-state laser devices such as Vertical Cavity Surface-Emitting Lasers (VCSELs), or Organic Light Emitting Diodes (OLEDs). The fundamental requirement for the excitation energy source(s) is that they emit suitable wavelengths for the excitation of the chosen phosphors or other luminescent materials (whose own emission wavelength ranges may in turn be chosen to excite a broad range of the fluorescent dyes typically used in fluorescence microscopy).

Figure 9:
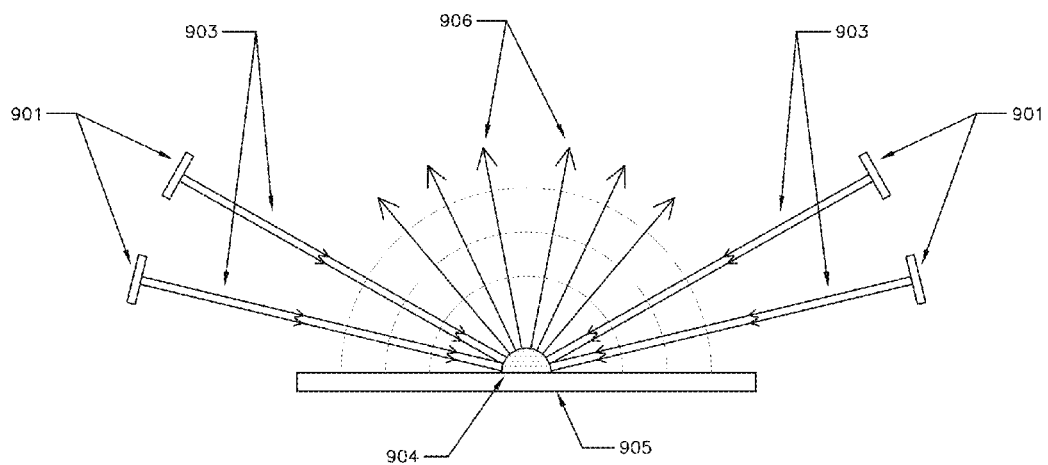
FIG. 9 shows another embodiment of the present invention, in which VCSEL excitation light sources are separated in space from the light-emitting phosphors or other luminescent material.

In the embodiment of the present invention shown in FIG. 9, one or more Vertical Cavity Surface-Emitting Lasers (VC-SELs) are used as the source of excitation energy for the blob of phosphors or other luminescent materials. One advantage for using VCSELs or other laser devices is that they emit a specific wavelength of light, and can be designed to provide suitable excitation wavelengths, matched to the types of phosphors or other luminescent materials used. Another advantage is that the light emitted by VCSELS or other laser devices is in the form of a narrow beam that can be directed at the phosphor blob without the need for collimating or focusing optics. FIG. 9 shows multiple VCSEL devices (901), with their light output (903) directed to a blob of phosphors or other luminescent materials (904). The multiple VCSEL devices shown on FIG. 9 are depicted as being spatially separated from each other. However, VCSELs are commonly implemented as densely-packed arrays of individual lasers, which emit light of their designed wavelength as multiple parallel beams. Thus, the one or more VCSEL devices (901) shown in FIG. 9 may actually comprise one or more VCSEL arrays, each of which emits multiple parallel beams of excitation light, aimed or directed at the blob of phosphors or other luminescent materials (904). In this way, high levels of excitation light may be directed at the phosphors or other luminescent materials, without the need for complex optics.

The present invention of a broad-spectrum illuminator for microscopy applications comprises a light source, as well as other optical elements for directing light into the microscope. The light source for the illuminator may be a densely packed LED, OLED or VCSEL chip array, with phosphors or other luminescent material, as shown and described in FIGS. 6A, 6B, 7A, and 7B. Alternatively, the light source for the illuminator may comprise a small area or "blob", or body of phosphors or other luminescent material, excited by LEDs, OLEDs or VCSEL light sources that are located away from the phosphors or other luminescent material, as shown in FIGS. 8 and 9. Regardless of the form of the light source, the overall illuminator is compact, and uses far fewer optical elements than the prior art LED illuminators which use multiple LED modules. The light emitting area of the light source is less than 15 mm, and typically in the range of 2-10 mm. For efficient coupling of light into the optics of the microscope, the light emitting area of the light source is preferably 2-4 mm. The number of wavelengths provided within the light source depends on the specific design of the light source, the choices of LEDs used in the light source, and the choices of phosphors or other luminescent materials used in the light source. A typical embodiment of the present invention would include at least four wavelengths of LEDs and/or phosphors, and might include as many as 8, 10, or even 12 wavelengths. Including more wavelengths within a single light source gives the users of the apparatus more choices of fluorescent molecules or dyes to use in their experiments, or it provides broad-spectrum white light of higher color rendering index, for brightfield applications. The multiple wavelengths, or a subset of them, may also be used simultaneously, in experiments that require the use of multiple, selectively-excited fluorescent dyes.

Generally speaking "broad-spectrum" would mean wavelengths that essentially filled (or provided good "coverage" of) the visible light spectrum of 400-700 nm. However, for brightfield applications, it is not really necessary to cover this whole range, and a somewhat reduced spectral range of (roughly) 450-650 nm would work. For fluorescent microscopy applications, the range of wavelengths needed would depend on the desired excitation wavelengths, for the dyes being used. This might call for wavelengths all the way down to 400 nm, or even a little lower (down to 350 nm in some cases).

Note that the above is referring to the light that is actually being delivered to the microscope. For the LED, OLED or VCSEL chips that are being used to excite the luminescent materials of the illuminator (either the "remotely located" LED, OLED or VCSEL chips that are exciting the luminescent body, or the LED, OLED or VCSEL chips that are underneath the luminescent layer), the wavelengths are a function of the specific luminescent materials being used. For most phosphors or other luminescent materials, the excitation wavelengths would be in the indigo to blue range, or the range of 410-490 nm. However, for fluorescent microscopy applications, one might need some wavelengths below 400 nm, as described above. And some longer-wavelength phosphors might benefit from being excited by LEDs with wavelengths above 490 nm, although most phosphors tend to have a fairly broad range of acceptable excitation wavelengths, and would fluoresce in response to light in the 410-490 nm wavelength range.

Figure 10:
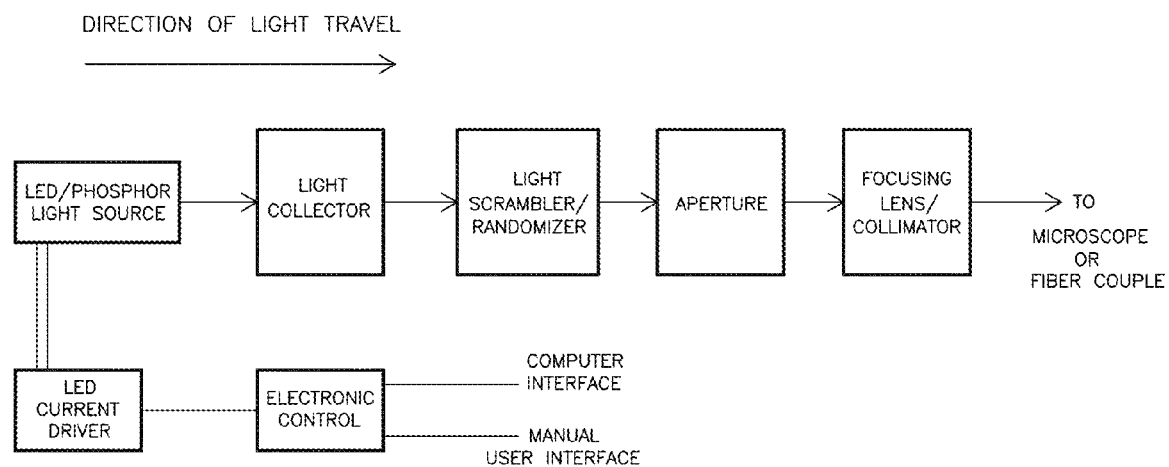
FIG. 10 is a block diagram representation of the illuminator of the present invention and illustrates the different components and their function in the apparatus.
Figure 11A:
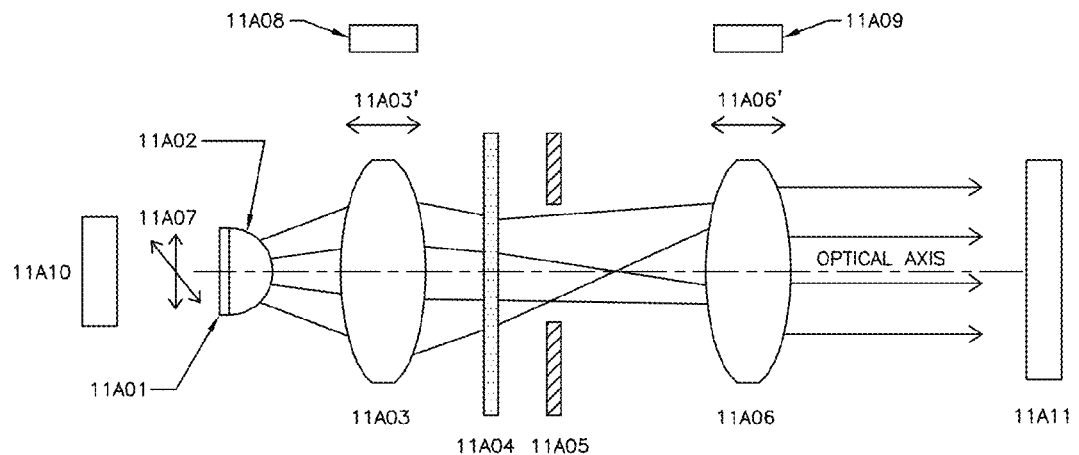
FIG. 11A is a representation of one embodiment of the present invention using a diffuser plate as a light scrambler/randomizer.

The light emitted by the phosphors, or other luminescent body of material, as shown in FIGS. 8 and 9 is light of multiple wavelengths or multiple wavelength ranges A schematic block diagram illustrating the major components in the apparatus of the present invention is shown in FIG. 10, with the optical elements of one embodiment shown in more detail in FIG. 11A. In these figures, the light source is depicted as an LED array, with phosphors or other luminescent materials applied on the surface of the LEDs. However, one skilled in the art will understand that the light source could also be in the form shown in FIGS. 8 and 9, in which a small area or "blob" of phosphors or other luminescent material is excited by remotely located LEDs or VCSELs.

The light emitted from the light source, whether the light source is an LED array assembly, or a "blob" of phosphors, has a Lambertian distribution. In the case of an LED array being used as the light source, as shown in FIG. 11A, a lens such as a half-ball lens (item 11A02) is attached to the top of the LED array (item 11A01) with a refractive index matching gel such as silicone filling the space between the LED chips and the half-ball lens, to reduce total reflection at the LED surfaces and improve light extraction. If the light source is a blob of phosphors or other luminescent material, the half ball lens may or may not be used. In any case, the diverging light from the light source is then immediately collected by a condensing lens (item 11A03) of high numerical aperture (small f-number). Afterwards, the light is homogenized using a light scrambler/randomizer, or diffuser (item 11A04). The aperture (item 11A05) serves to define the shape and size of the beam, and also blocks light that is less well-mixed at the perimeter of the beam. The combination of the light scrambler/homogenizer (or diffuser) and the aperture ensures that the resulting intensity distribution is uniform over the illuminated area entering the microscope and over a broad spectrum. The light scrambler (item 11A04) can be any kind of material that evenly distributes light, for instance by having randomly textured surfaces or imbedded diffractive particles. In one embodiment of the present invention, an engineered diffuser is used, that provides a non-Gaussian, circular "top-hat" beam pattern, with a flatter beam intensity profile than would be obtained from a traditional diffuser. This form of diffuser aids in achieving a highly uniform beam pattern. Said "top-hat" diffusers are available from multiple vendors, and achieve their shaped beam profile, with a high degree of beam uniformity, through the use of an engineered surface, consisting of a large number of microlenses. These microlenses are fabricated with a known pattern to create the desired overall beam shape, but the parameters of the individual microlenses are randomized in order to create a diffuse beam that is relatively insensitive to the spatial characteristics of the input beam. These engineered diffusers are available in a variety of beam shapes, including circular beams, square beams, and line-shaped beams, all with good uniformity. The type used in one embodiment of the present invention provides a circular beam.

Figure 11B:
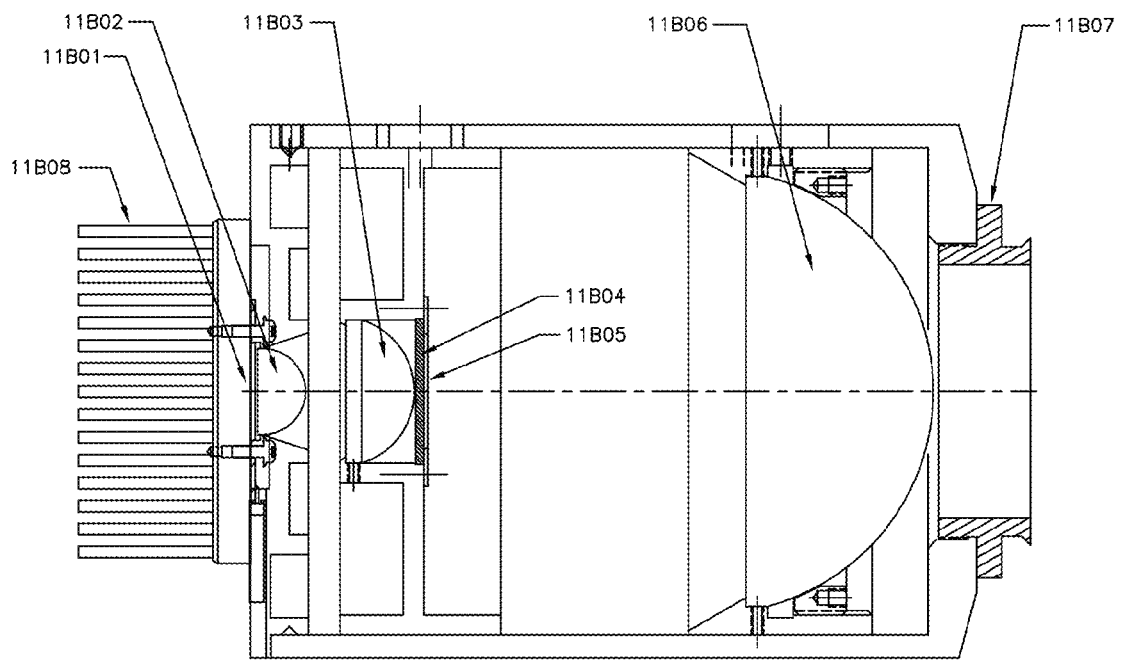
FIG. 11B shows a cross-section view of the optical elements of one practical implementation of one embodiment of the present invention.

A focusing lens/collimator of relatively large aperture and diameter (item 11A06) is placed at the end of the light path before entering the microscope. Though not described in detail, other kinds of lenses that improve light extraction, collection, and collimation are within the scope of the present invention. FIG. 11B provides a cross-section view of the optical elements of one embodiment of the present invention in which a plano-convex lens (item 11B03) and diffuser plate (item 11B04) are used as the light collector and scrambler, respectively. In the embodiment shown in FIGS. 11A and 11B, the positions of both the light collector lens (items 11A03 and 11B03) and the focusing lens/collimator (items 11A06 and 11B06) can be adjusted slightly along the optical axis. This adjustability is used to optimize the optical performance of the apparatus, to work with different brands of microscopes. Note that items 11B01 through 11B06 of FIG. 11B correspond to the similarly numbered items 11A01 through 11A06 of FIG. 11A. In addition, FIG. 11B shows a representative mounting adaptor (11B07), used to mount the illuminating apparatus to the microscope. It also shows a heat spreader and heat sink (11B08) mounted to the back side of the LED array (11B01).

Figure 12A:
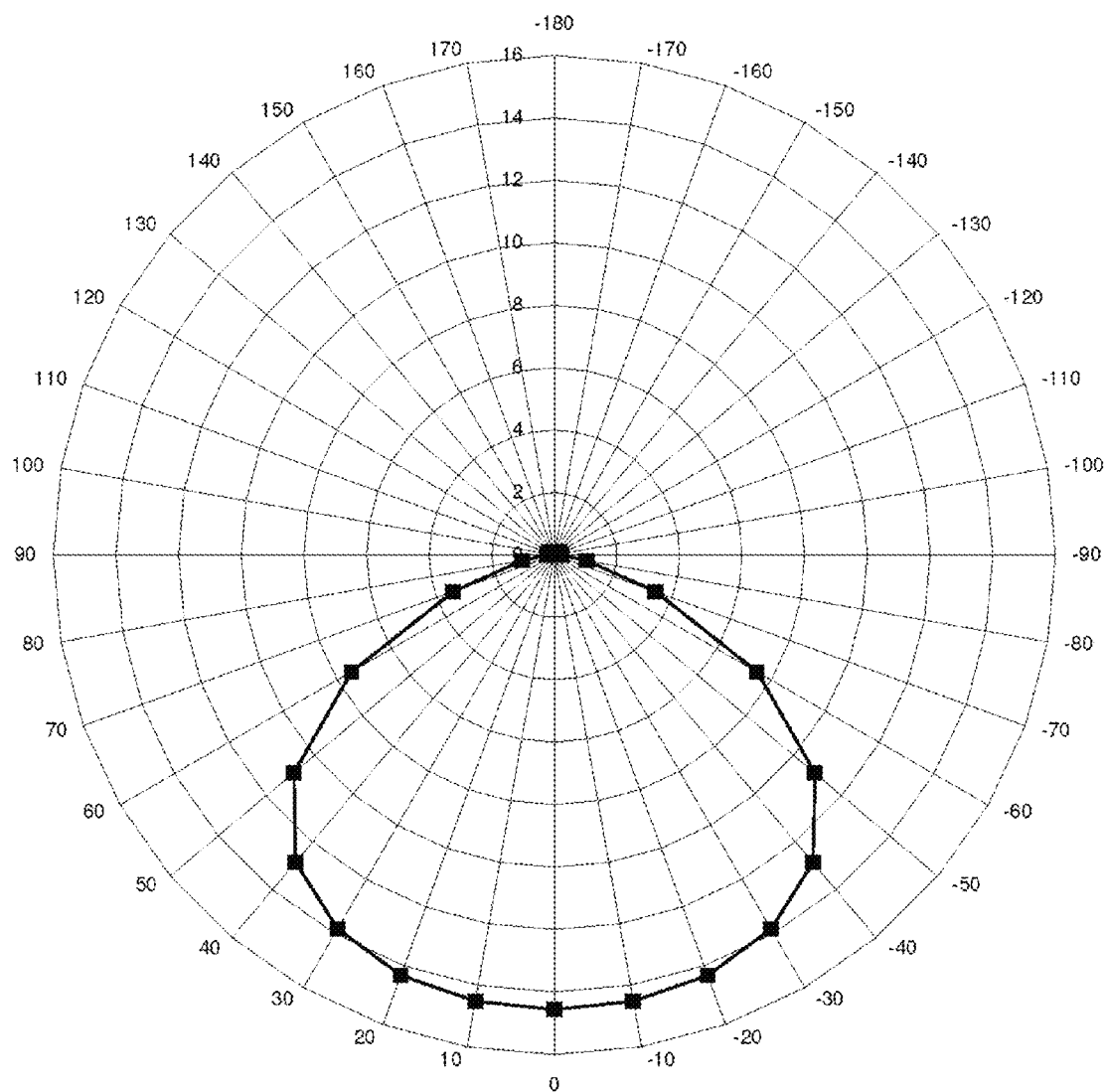
FIGS. 12A and 12B show polar and rectangular coordinate plots of the light output of the LED array used in one embodiment of the present invention, including the half-ball lens that sits over the LED array.
Figure 12B:
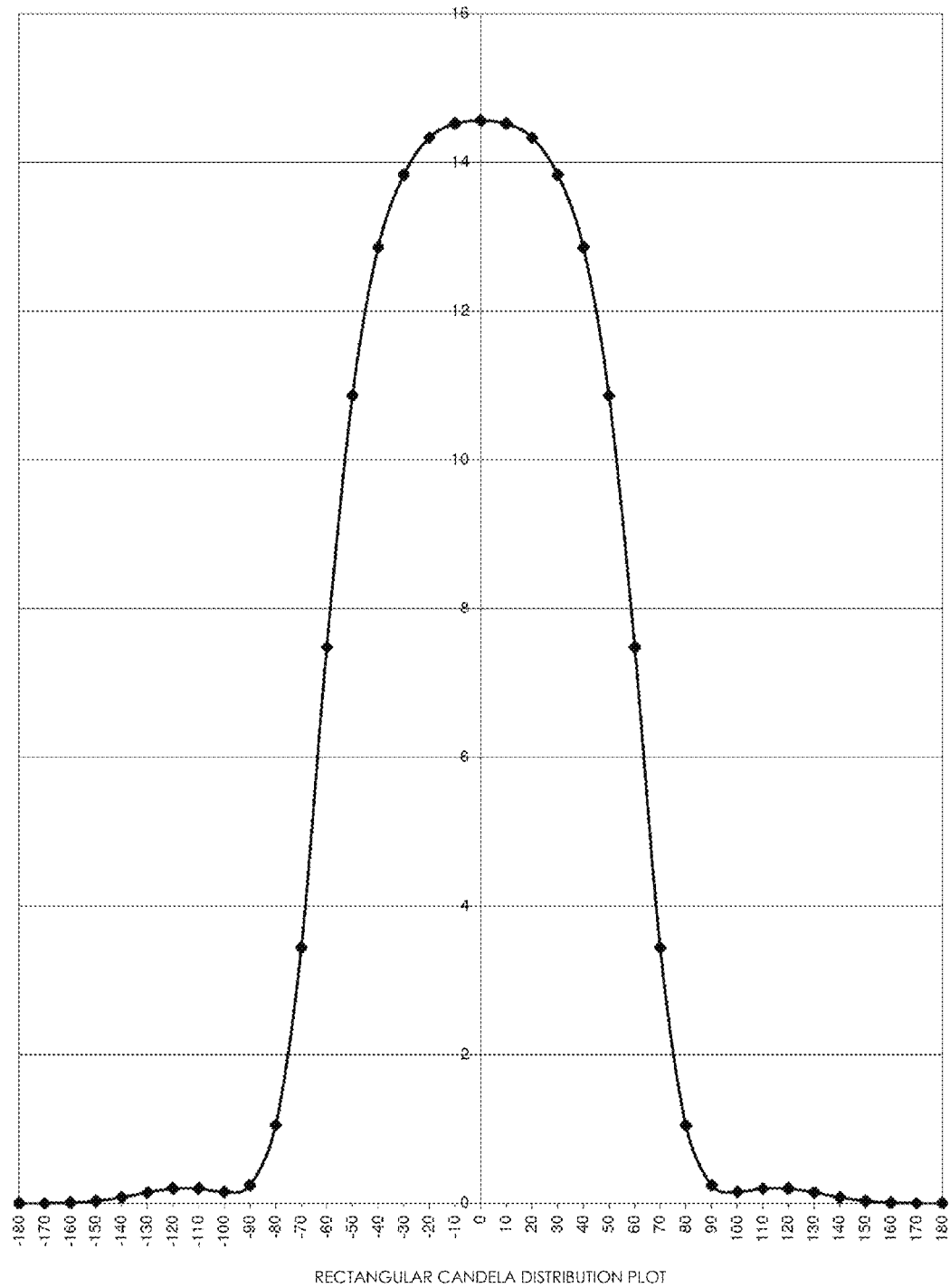
Figure 12C:
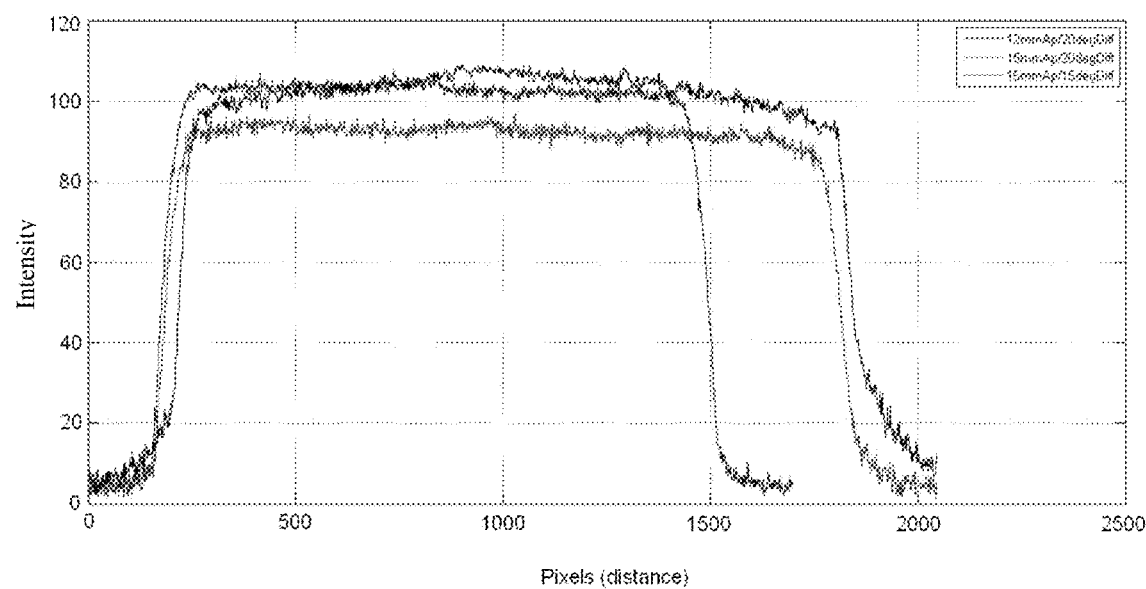
FIG. 12C provides plots of the light uniformity of the beam that exits the optical elements of one embodiment of the present invention, showing the relative effects of different aperture dimensions and different diffusers.

FIGS. 12A and 12B provide polar and rectangular coordinate plots of the light output of the LED array used in one embodiment of the present invention, including the half-ball lens that is affixed to the surface of the LED array. As can be seen in these figures, the LED array and half-ball lens provide a fairly wide beam, but with insufficient uniformity of light intensity across the beam. In contrast, FIG. 12C shows several plots of the light intensity across the beam that is emitted from the entire apparatus of one embodiment of the present invention. The three plots of FIG. 12C represent differing combinations of aperture diameter and the angle of the diffuser element. As expected the plot obtained with an aperture of 12 mm diameter shows a narrower beam, compared to the plots taken with an aperture of 15 mm. But in all cases, the beam is highly uniform, with sharply-defined beam boundaries.

Figure 13A:
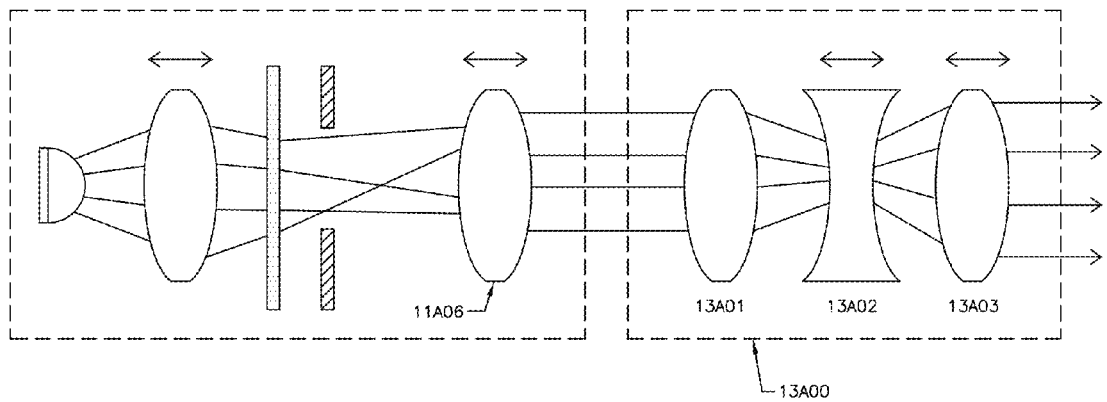
FIG. 13A is a schematic view of one embodiment where the light coming from the embodiment in FIG. 11 is sent into a zoom lens system to expand or contract the beam width.
Figure 13B:
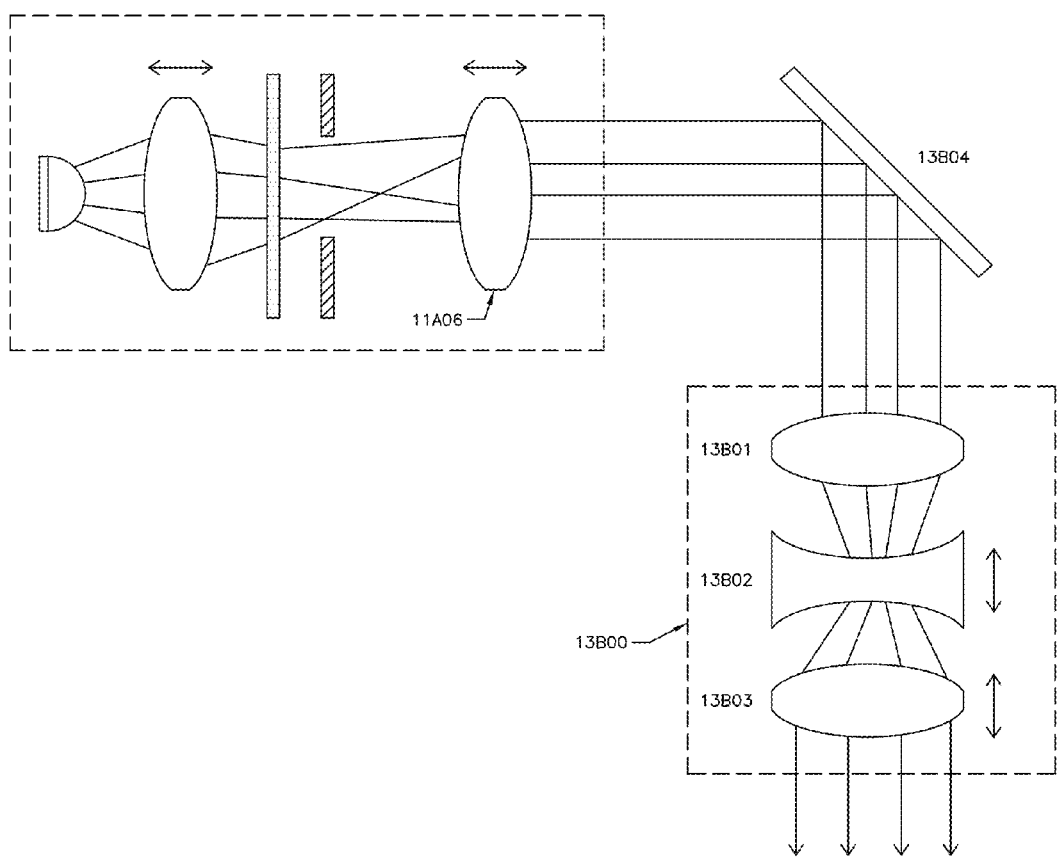
FIG. 13B is a schematic view of another embodiment where a mirror is placed between the embodiment in FIG. 11 and zoom lens system shown in FIG. 13A to redirect the light path.

The described embodiments of the present invention produce an intense and uniformly illuminated area which can be either sent directly into the microscope or to other optical elements for further beam shaping. FIG. 13A illustrates one embodiment in which a beam expander (items 13A01-13A03) is placed after the collimating/focusing lens. FIG. 13B illustrates the same embodiment of the apparatus except that a mirror (item 13B04) is placed between the collimating lens/focusing lens and beam expander to change the geometry of the light path, which may make packaging more convenient and compact. Although not shown in any of the figures except for FIG. 11B, the apparatus of the present invention can be fitted with a variety of mounting adapters, intended to mate mechanically with the optical ports of multiple brands of microscopes.

Figure 14:
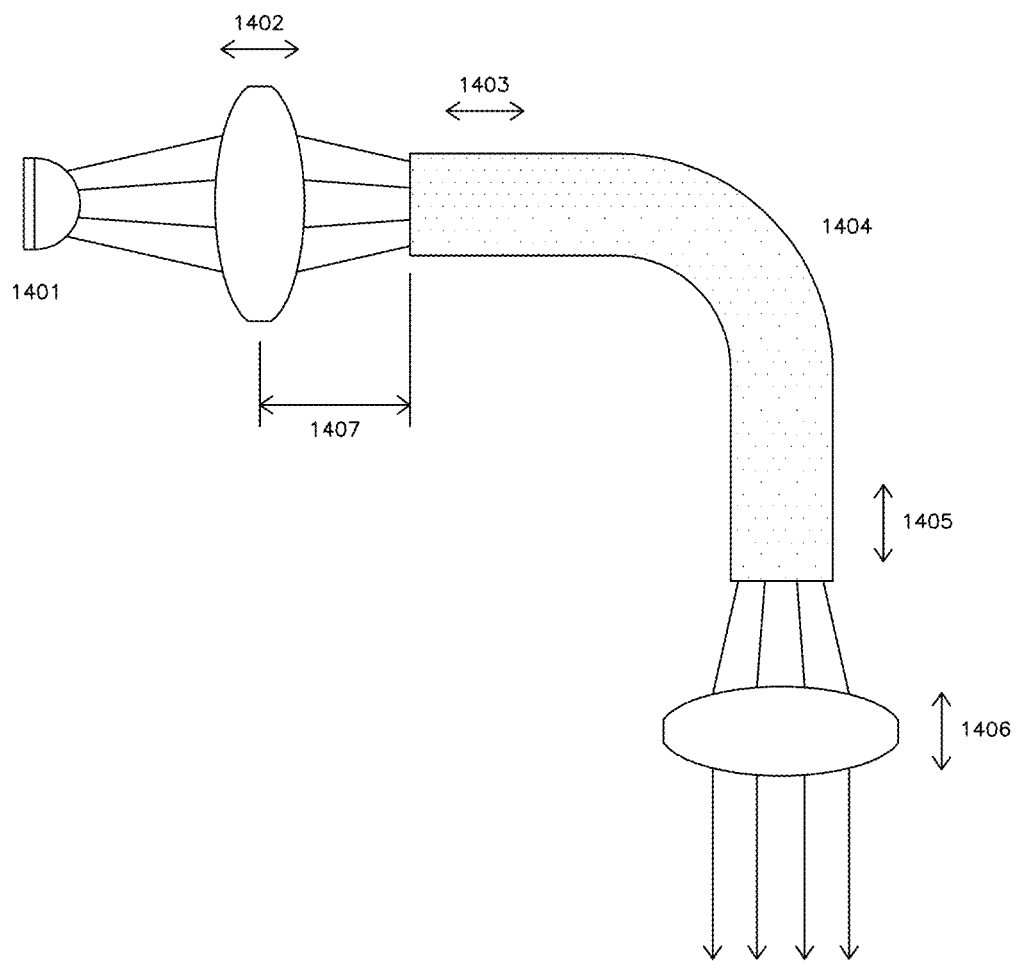
FIG. 14 is a schematic view of yet another embodiment of the present invention, using a light mixing tube as a light scrambler/randomizer and the variable distance between the collector lens and tube entrance as a means to change the effective aperture size.

FIG. 14 illustrates one embodiment of the present invention using a light mixing tube as a light scrambler/randomizer, and makes use of a variable distance between the collector lens and tube entrance as a means of changing the effective aperture size. The light mixing tube (item 1404), typically constructed of acrylic with many small diffractive particles embedded, can be used in place of the diffuser and aperture shown in FIGS. 11A and 11B. Similar to a fiber, the separation distance (shown as item 1407) between the collecting lens (item 1402) and light mixing tube, determines the accepting angle of the mixing tube and hence acts like a variable aperture that can be adjusted.

Figure 15:
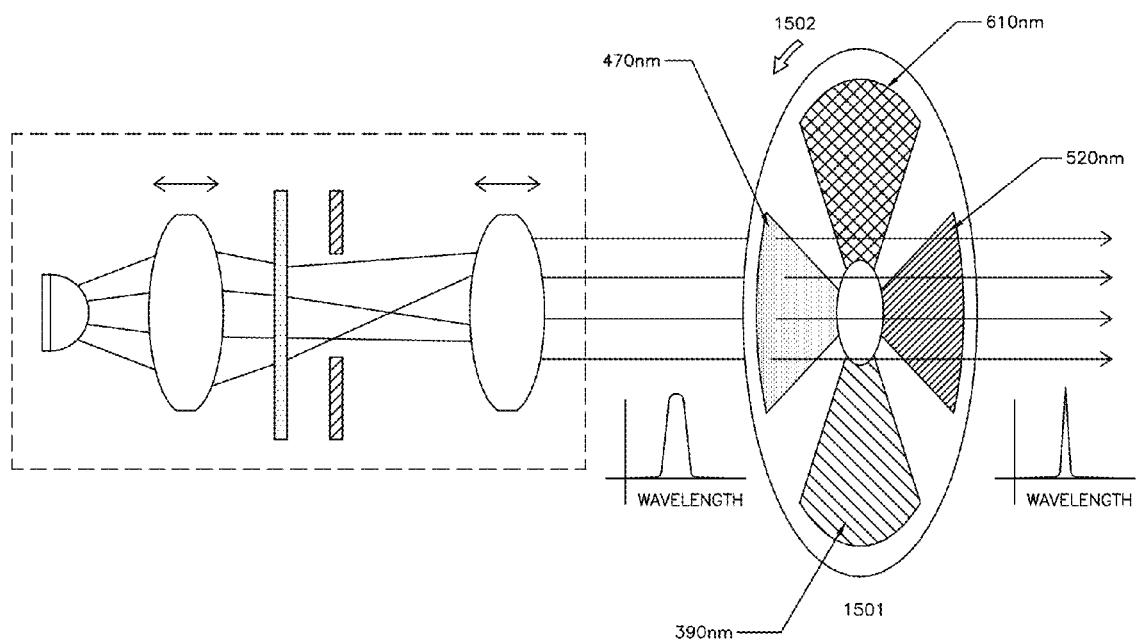
FIG. 15 is a representation of one embodiment of the present invention that uses a narrow bandpass filter wheel, following the embodiment of FIG. 11, to either select a specific wavelength range, or to further narrow the bandwidth of the selected wavelength range.

Aside from elements such as lenses and light scramblers which can reshape the size or spatial distribution of the light, other optical elements can be used to modify the spectral distribution of the light as well. Numerous fluorescence applications benefit from having exceptionally narrow bandwidths, so narrow bandpass filters can be used to further reduce the spectral distribution of the LED chip(s), and/or the phosphors or other luminescent materials that are used in the light source. To the extent that the light source is emitting broad-spectrum light, consisting of multiple wavelengths or wavelength ranges as components of the light, the use of narrow bandpass filters may be required for fluorescence microscopy applications. FIG. 15 illustrates one embodiment of the present invention that uses narrow bandpass filters on a filter wheel. Current filter technology can reduce the bandwidth to be less than 1.0 nm. Since the filter does cut off some optical power, the choice of filters and whether or not to use them at all will depend on the users' preference between having a narrower bandwidth versus maximally intense light.

The present invention includes a set of LED current driver circuits, and electronic control, as shown in FIG. 10. The purpose of the LED current drivers is to convert the DC voltage provided by the apparatus' AC-to-DC power supply, to a constant DC current for each of the strings of LED chips in the LED array. For example, with the LED array configuration of FIGS. 6A and 6B, with four wavelengths or colors of LED chips (or four possible combinations of LED wavelength and phosphor emission), the apparatus could have four LED current driver circuits, each feeding a constant DC current to one of the LED chips within the LED array. Note that if the LED array has a larger number of LED chips, multiple LED chip sites could be tied together as series strings of LEDs, with each LED current driver circuit driving a series string comprising multiple LED chips.

The electronic control circuitry shown in FIG. 10 performs several functions. The primary function of the electronic control is to turn on and off, as well as control the brightness of, each of the LED colors or wavelengths embodied in the LED array. This is done by directing the LED current driver circuits to either source a constant DC current, or to turn off the current flow. Brightness control of the LEDs is obtained by changing the value of the DC current that each LED current driver circuit provides. If phosphors or other luminescent material has been applied on top of the LED chips, then control of the brightness of the LED chip, or chips, will also control the brightness of the emissions from the overlaying phosphors or other luminescent materials. In the case of the light source being a "blob" of phosphors, that is excited by remotely-located LEDs or VCSELs, the brightness of the emissions from the phosphors is controlled by controlling the brightness of the exciting LEDs or VCSELs. In this case, there will be less ability to control the individual emissions from specific phosphors, unless the specific phosphors are excited by different wavelengths of excitation light, from the remotely-located LEDs or VCSELs.

As shown in FIG. 10, user input to the electronic control circuitry of the present invention can via a computer interface, or via manual user interface. In one embodiment, the computer interface is via a USB port. Software that is resident on a user's computer will send command messages via the USB interface, to the electronic control circuitry of the present invention. A microprocessor within the electronic control circuitry, running embedded software or firmware, will interpret the messages sent from the user's computer, in order to control the states of the illuminator apparatus. The manual user interface uses a combination of switches, knobs, and a dedicated display, to allow the user to select the color(s) or wavelength(s) of the illuminator apparatus, and the brightness of the LEDs, without requiring a separate computer.

Through the use of the USB interface, a separate computer can be used to turn on and off the individual LED chips or strings of LED within the LED array at a rapid rate, thereby also turning on and off the different wavelengths or wavelength ranges of the LED chips, and any overlaying phosphors, limited by the speed at which the processor within the electronic control circuitry of the present invention is able to process the commands received over the USB interface. For even faster response, in the sub-microsecond range, one embodiment of the electronic control circuitry has direct digital and analog inputs, that can be used to directly turn on and off the selected wavelength's (or wavelength range's) LED current driver circuit, or, alternatively, to directly set the brightness level of the selected wavelength or wavelength range. Switching from one wavelength to another wavelength is limited by the processing speed of the microprocessor within the electronic control circuitry. In the case of a broad-spectrum light source, with the wavelength or wavelength range being selected via use of external narrow-bandpass filters (as in the embodiment shown in FIG. 15), the speed of wavelength switching is a direct function of the speed at which the external filters can be changed, either manually, or via such mechanisms as a motorized "color wheel".

The invention claimed is:
1. A broad-spectrum, multiple wavelength illuminator for providing light along an optical axis, comprising:
   a luminescent body;
   a plurality of LED chips or arrays of LED chips emitting light within one or more wavelength ranges towards said luminescent body, causing said luminescent body to emit light of one or more wavelength ranges, said plurality of LED chips or arrays of LED chips spaced apart from said luminescent body;
   a plurality of optical devices, each of the optical devices focusing light emitted from a corresponding one of the LED chips or arrays of LED chips onto the luminescent body;

an optical element adjacent to the luminescent body that collects light emitted by the luminescent body; and an optical device that collects and directs light emitted by the luminescent body and collected by said optical element along said optical axis.

2. The illuminator of claim 1, said plurality of LED chips or arrays of LED chips spaced apart from said luminescent body by at least 2 mm.

3. The illuminator of claim 1, said plurality of LED chips or arrays of LED chips including organic light emitting diodes.

4. The illuminator of claim 3, wherein said luminescent body emits light from a light emitting area having a diameter that is not more than 15 mm.

5. The illuminator of claim 3, wherein said luminescent body emits light from a light emitting area having a diameter that is in a range of about 2-10 mm.

6. The illuminator of claim 3, wherein said luminescent body emits light from a light emitting area having a diameter that is in a range of about 2-4 mm.

7. The illuminator of claim 1, wherein said at least some of the LED chips or arrays of LED chips emit light in the indigo to blue wavelength range.

8. The illuminator of claim 1, said luminescent body comprising one or more types of phosphors or quantum dots, emitting light of one or more wavelength ranges.

9. The illuminator of claim 1, said luminescent body emitting light of substantially uniform intensity across a broad spectrum, including the range of about 400-700 nm.

10. The illuminator of claim 1, said luminescent body emitting light of multiple wavelengths or multiple wavelength ranges.

11. The illuminator of claim 1, further comprising an aperture located in the optical axis between the optical element and the optical device passing the light emitted by the luminescent body along said optical axis, wherein light collected by said optical element and said optical device and passed by the aperture forms a beam of light illuminating a target.

12. The illuminator of claim 1, further comprising a reflector that supports the luminescent body and that reflects light emitted by said plurality of LED chips or arrays of LED chips towards said optical element, said optical element collecting and directing light emitted by the plurality of LED chips or arrays of LED chips and light emitted by the luminescent body along said axis towards an aperture and said optical device.

13. The illuminator of claim 12, wherein the light emitted by the plurality of LED chips or arrays of LED chips supplements the light emitted by the luminescent body to provide light of substantially uniform intensity across a broad spectrum.

14. The illuminator of claim 1, further comprising a diffusing/scattering/homogenizing element located in a path of the beam between the luminescent body and the aperture so that the beam illuminating the target is substantially spectrally uniform across an area of the target illuminated by the beam.

15. A method for providing light along an optical axis, comprising:
    causing a plurality of LED chips or arrays of LED chips to emit light within different wavelength ranges towards a luminescent body spaced apart from said plurality of LED chips or arrays of LED chips;
    using each of a plurality of optical devices to focus light emitted from a corresponding one of the LED chips or arrays of LED chips onto the luminescent body, causing said luminescent body to emit light; and
    collecting light emitted by the luminescent body;
    passing the light collected from the luminescent body through an aperture to form a beam along the optical axis; and
    collimating the beam and directing the collimated beam along said optical axis to a target.

16. The method of claim 15, wherein said luminescent body is caused to emit light of substantially uniform intensity across a broad spectrum, including the range of about 400-700 nm.

17. The method of claim 15, wherein said luminescent body is caused to emitting light of multiple wavelengths or multiple wavelength ranges.

18. The method of claim 15, further comprising reflecting light emitted by said plurality of LED chips or arrays of LED chips, wherein said collecting collects and said collimating and directing collimates and directs said reflected light from the plurality of LED chips or arrays of LED chips and light emitted by the luminescent body along said axis towards said target.

19. The illuminator of claim 18, wherein said at least some of the LED chips or arrays of LED chips emit light in the 410-490 nm wavelength range.

20. The method of claim 18, wherein the light emitted by the plurality of LED chips or arrays of LED chips supplements the light emitted by the luminescent body to provide light of substantially uniform intensity across a broad spectrum.

21. A broad-spectrum, multiple wavelength illuminator for providing light along an optical axis, comprising:
    a luminescent body;
    a plurality of vertical cavity surface emitting laser chips emitting light within one or more wavelength ranges towards said luminescent body along different optical paths without any optical elements in said optical paths, causing said luminescent body to emit light of one or more wavelength ranges, said plurality of vertical cavity surface emitting laser chips spaced apart from said luminescent body; and
    an optical element adjacent to the luminescent body that collects light emitted by the luminescent body; and
    an optical device that collects and directs light emitted by the luminescent body and collected by said optical element along said optical axis.

22. A broad-spectrum, multiple wavelength illuminator for providing light along an optical axis, comprising:
    a luminescent body emitting light from a light emitting area having a diameter that is in a range of about 2-10 mm;
    a plurality of semiconductor chips emitting light within one or more wavelength ranges towards said luminescent body along directions away from said optical axis, causing said luminescent body to emit light of one or more wavelength ranges, said plurality of semiconductor chips spaced apart from said luminescent body;
    an optical element adjacent to the luminescent body that collects light emitted by the luminescent body; and
    an optical device that collects and directs light emitted by the luminescent body and collected by said optical element along said optical axis.

23. The illuminator of claim 22, wherein said luminescent body is supported on a surface that is not a mirror.

24. The illuminator of claim 22, wherein said luminescent body is on said optical axis, said plurality of semiconductor chips emitting light towards said luminescent body along directions away from said optical axis.

25. The illuminator of claim 22, said plurality of semiconductor chips including vertical cavity surface emitting laser chips, wherein light provided by said vertical cavity surface emitting laser chips is directed to the luminescent body along an optical path without any optical element in said optical path.

26. The illuminator of claim 22, said optical element comprising a half ball lens, said optical device comprising a second lens collecting light collected by the half ball lens, said illuminator further comprising an aperture that passes and shapes the light collected by the second lens into a beam and a third lens focusing the beam to a target.

27. The illuminator of claim 26, further comprising a diffusing/scattering/homogenizing element located in a path between the luminescent body and the aperture so that the light illuminating the luminescent body is substantially spectrally uniform across an area of the luminescent body.

28. A broad-spectrum, multiple wavelength illuminator for providing light along an optical axis, comprising:
- a luminescent body comprising different regions containing different luminescent materials or different mixtures of luminescent materials;
- a plurality of semiconductor chips emitting light within one or more wavelength ranges towards said luminescent body along directions away from said optical axis, causing the different regions of said luminescent body to emit light of different wavelength ranges, said plurality of semiconductor chips spaced apart from said luminescent body;
- an optical element adjacent to the luminescent body that collects light emitted by the luminescent body; and
- an optical device that collects and directs light emitted by the luminescent body and collected by said optical element along said optical axis.

* * * * *